295B2

(12) United States Patent
Cayli

(10) Patent No.: US 8,426,202 B2
(45) Date of Patent: Apr. 23, 2013

(54) CELL CULTURE MEDIUM

(75) Inventor: Aziz Cayli, Ulm (DE)

(73) Assignee: Cellca GmbH (DE)

( * ) Notice: Subject to any disclaimer, the term of this patent is extended or adjusted under 35 U.S.C. 154(b) by 793 days.

(21) Appl. No.: 12/067,878

(22) PCT Filed: Sep. 8, 2006

(86) PCT No.: PCT/EP2006/008761

§ 371 (c)(1),
(2), (4) Date: Mar. 24, 2008

(87) PCT Pub. No.: WO2007/036291

PCT Pub. Date: Apr. 5, 2007

(65) Prior Publication Data

US 2008/0254513 A1    Oct. 16, 2008

(30) Foreign Application Priority Data

Sep. 28, 2005   (DE) .......................... 10 2005 046 225

(51) Int. Cl.
   C12N 5/02      (2006.01)
(52) U.S. Cl.
   USPC ............................. 435/404; 435/41; 435/70.1
(58) Field of Classification Search .................... 435/41, 435/70.1, 404
   See application file for complete search history.

(56) References Cited

U.S. PATENT DOCUMENTS

| | | | |
|---|---|---|---|
| 4,049,494 A | 9/1977 | Tomei | |
| 5,661,034 A * | 8/1997 | Hayakawa et al. | 435/383 |
| 6,048,728 A * | 4/2000 | Inlow et al. | 435/404 |
| 7,390,660 B2 | 6/2008 | Behrendt et al. | |
| 7,405,068 B2 | 7/2008 | van Maris et al. | |
| 2003/0059935 A1 | 3/2003 | Kikuchi et al. | |
| 2003/0096402 A1* | 5/2003 | Lee et al. | 435/325 |
| 2004/0048368 A1 | 3/2004 | Chen et al. | |

FOREIGN PATENT DOCUMENTS

| | | |
|---|---|---|
| DE | 29 46 898 | 6/1980 |
| EP | 0 338 841 A1 | 10/1989 |
| EP | 0 435 911 B1 | 7/1991 |
| EP | 0 659 880 B1 | 6/1995 |
| EP | 1 342 780 A1 | 9/2003 |
| JP | 05 308962 | 11/1993 |
| JP | 2003-250533 | 9/2003 |
| SU | 663712 A * | 5/1979 |
| WO | WO 98/41611 | 9/1998 |
| WO | WO 03/064630 A2 | 8/2003 |
| WO | WO 03/106661 A2 | 12/2003 |
| WO | WO 2004/024899 | 3/2004 |
| WO | WO 2004/099425 A2 | 11/2004 |

OTHER PUBLICATIONS

Ain et al. Succinate and Malate Improve Development of Hamster Eight-Cell Embryos In Vitro: Confirmation of Viability by Embryo Transfer. Mol. Reprod. Dev. 47:440-447, 1997.*
Waymouth, C. Osmolality of Mammalian Blood and of Media for Culture of Mammalian Cells, In Vitro 6:109-127 (1970).*
Ludwig et al. Differential Effect of Hexoses on Hamster Embryo Development in Culture. Biology of Reproduction 64, 1366-1374 (2001).*
MSDS for succinic acid by JTBaker. 2010. downloaded from http://www.jtbaker.com/msds/englishhtml/S7226.htm. p. 1-2.*
International Search Report and Written Opinion dated May 30, 2007 issued in corresponding PCT Application No. PCT/EP2006/008761.
Database WPI Week 199401 Derwent Publications Ltd., London, GB; AN 1994-002164 XP002433427, Nov. 22, 1993 Abstract for JP05-308362 (JP1992-147005).
Notice of Reasons for Rejection mailed Jan. 31, 2012 in corresponding Japanese Patent Application No. 2008-532622 (with English translation).
J. M. Renard, et al., "Evidence That Monoclonal Antibody Production Kinetics is Related to the Integral of the Viable Cells Curve in Batch Systems," Biotechnology Letters, 1988, 10(2), pp. 91-96.
Kevin J. Verstrepen, et al., "Glucose and Sucrose: Hazardous Fast-Food for Industrial yeast?," Trends in Biotechnology, Oct. 2004, 22 (10), pp. 531-537.
Jörg Neerman, et al., "Comparative Analysis of Glucose and Glutamine Metabolism in Transformed Mammalian Cell Lines, Insect and Primary Liver Cells," Journal of Cellular Physiology, 1996, 166 (1), pp. 152-169.
Anna F. Europa, et al., "Multiple Steady States With Distinct Cellular Metabolism in Continuous Culture of Mammalian Cells," Biotechnology and Bioengineering, Jan. 5, 2000, 67(1), pp. 25-34.
Anna Sanfeliu, et al., "Effect of Glutamine Limitation on the Death of Attached Chinese Hamster Ovary Cells," Biotechnology and Bioengineering, Jul. 5, 1999, 64(1), pp. 46-53.
Dr. Sevim Duvar, et al., "Production of Bio-pharmaceuticals With Animal Cells," Transkript, Laborwelt 2004, 5(1), pp. 34-36.
Keqin Chen, et al., "Engineering of a Mammalian Cell Line for Reduction of Lactate Formation and High Monoclonal Antibody Production," Biotechnology and Bioengineering, Jan. 5, 2001, 72:1, pp. 55-62.
Noushin Irani, et al., "Improvement of the Primary Metabolism of Cell Cultures by Introducing a New Cytoplasmic Pyruvate Carboxylase Reaction," Biotechnology and Bioengineering, 1999, 66:4, pp. 238-246.
C. Altamirano, et al., "Improvement of CHO Cell Culture Medium Formulation: Simultaneous Substitution of Glucose and Glutamine," Biotechnol. Progress, 2000, 16(1), pp. 69-75.
C. Altamirano, et al., "Decoupling Cell Growth and Product Formation in Chinese Hamster Ovary Cells Through Metabolic Control," Biotechnology and Bioengineering, Dec. 2001, 76(4), pp. 351-360.
C. Altamirano, et al., "Strategies for Fed-Batch Cultivation of t-PA Producing CHO Cells: Substitution of Glucose and Glutamine and Rational Design of Culture Medium," Journal of Biotechnology, 2004, 110(2): pp. 171-179.
Stephen M. Downs, et al., "Energy Substrates and the Completion of Spontaneous Meiotic Maturation," Zygote, Nov. 2000, 8(4), pp. 339-351.

(Continued)

*Primary Examiner* — Taeyoon Kim
(74) *Attorney, Agent, or Firm* — Ostrolenk Faber LLP

(57) ABSTRACT

The invention relates to nutrient media, in particular cell culture media, which contain at least one substance selected from the group comprising citric acid, succinic acid, malic acid, α-keto-glutaric acid, fumaric acid, oxalacetic acid, isocitric acid, oxalosuccinic acid, tartaric acid, lactic acid, adipic acid and mixtures thereof and salts, derivatives or complexes of these acids. The invention further relates to the use and methods of production of said cell culture media, methods of cultivation of a cell culture in a cell culture medium according to the invention and cells that can be obtained by said methods.

8 Claims, 9 Drawing Sheets

OTHER PUBLICATIONS

Figure 1:
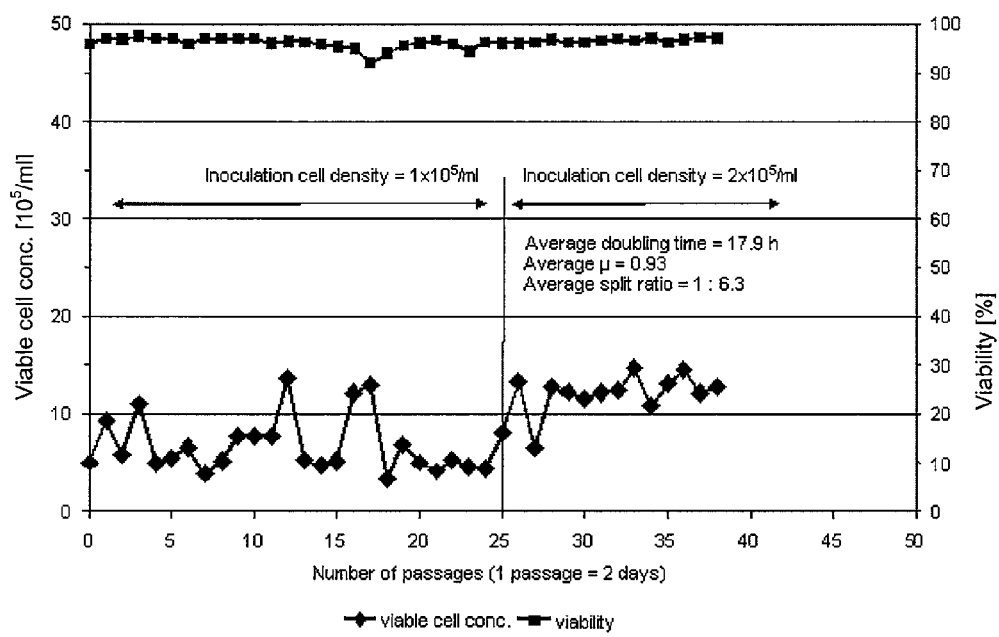

T. Hassel, et al. "Adaptation to Non-Ammoniagenic Medium and Selective Substrate Feeding Lead to Enhanced Yields in Animal Cell Cultures," Journal of Cell Science, 1990, 96 (Pt3), pp. 501-508.

Frank Deer, et al., "Novel Fed-Batch Strategy for CHO Cell Culture," Genetic Engineering News, Apr. 1, 2000, 20(7), p. 42.

N. Kurano, et al., "Growth Behavior of Chinese Hamster Ovary Cells in a Compact Loop Bioreactor. 2. Effects of Medium Components and Waste Products," 1990, Journal of Biotechnology, 15(1-2), pp. 113-128.

E. Roth, et al., "Influence of Two Glutamine-Containing Dipeptides on Growth of Mammalian Cells," In Vitro Cellular & Developmental Biology, Jul. 1988, 24(7), pp. 696-698.

A. Christie, et al., "Glutamine-Based Dipeptides are Utilized in Mammalian Cell Culture by Extracellular Hydrolysis Catalyzed by a Specific Peptidase," Journal of Biotechnology, 1994, 37(3), pp. 277-290.

Ch. Depre, et al., "Role of Fructose 2,6-Biphosphate in the Control of Glycolysis. Stimulation of Glycogen Synthesis by Lactate in the Isolated Working Rat Heart," Acta Cardiologica, 1993, 48(1), pp. 147-164.

Ovchinnikov, I.V., et al., Ukrainskii Biokhimicheskii Zhurnal, 1985, 57(4), pp. 72-75.

Rupasri Ain, et al., "Succinate and Malate Improve Development of Hamster Eight-Cell Embryos In Vitro: Confirmation of Viability by Embryo Transfer," Molecular Reproduction and Development, 1997, 47(4), pp. 440-447.

Pelin Faik, et al., "A Method for the Isolation of Chinese Hamster Cell Variants With an Altered Ability to Utilise Carbohydrates," Cell Biology International Reports, 1977, 1(6), pp. 555-562.

* cited by examiner

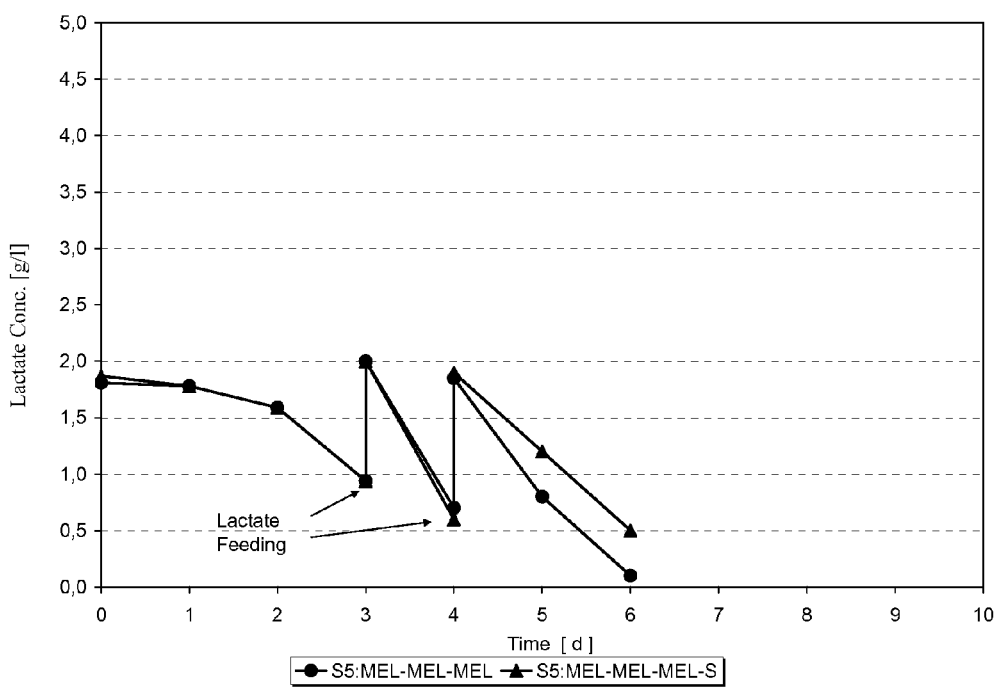

CELL CULTURE MEDIUM

CROSS REFERENCE TO RELATED APPLICATIONS

The present application is a 35 U.S.C. §§371 national phase conversion of PCT/EP2006/008761, filed Sep. 8, 2006, which claims priority of German Patent Application No. 10 2005 046 225.1, filed September 28, 2005, the disclosure of which has been incorporated herein by reference. The PCT International Application was published in the German language.

TECHNICAL FIELD

The present invention relates to a nutrient medium, in particular a cell culture medium, for the cultivation of at least one cell and/or for obtaining a polypeptide, protein and/or a vaccine from organisms, in particular from cells or from cell cultures, the organisms being cultivated in the nutrient medium according to the invention, and the desired polypeptide, protein or vaccine being obtained from the organisms and/or the culture supernatant.

It was found, surprisingly, that the addition of organic acids or salts, derivatives or complexes of organic acids, selected from the group comprising citric acid, succinic acid, malic acid, α-keto-glutaric acid, fumaric acid, oxalacetic acid, isocitric acid, oxalosuccinic acid, tartaric acid, adipic acid, lactic acid to a nutrient medium increased the growth and/or the productivity of the cells and/or reduced the formation of toxic metabolites. The increase in productivity and/or decrease in formation of by-products produced according to this aspect of the invention can be achieved if the substances according to the invention are added on their own to a nutrient medium, in particular a cell culture medium, or are combined with one another, or are combined with other carbohydrates, in particular if the substances are added to a medium containing little if any glutamine, or are used with a medium that contains glutamine substitutes.

The substances according to the invention are used as modulators of cell metabolism. They act as additional sources of energy and/or carbohydrates. In this connection the substances can be used in a nutrient medium, in particular in a cell culture medium, at correspondingly higher concentration, which contains carbohydrates and/or glutamine. The substances according to the invention can, however, also be used in a nutrient medium, in particular in a cell culture medium, containing no carbohydrates and/or no glutamine.

STATE OF THE ART

Animal cells, in particular mammalian cells, are being used increasingly as host cells in the production of vaccines, for example viruses or polypeptides. Continuously growing cells are generally used for this, i.e. cell lines that are either immortalized cells or tumor cells. For some applications, primary cells are used, which are taken for example directly from humans or animals. There are large differences between primary cells and cell lines, when they are cultivated in vitro. The primary cells can only divide a few times, whereas cell lines can divide practically infinitely often. There can also be a difference in cell metabolism between primary cells and permanent cell lines, for example glucose consumption rate, lactate formation rate and glutamine consumption rate.

One objective of process optimization in the use of cells, in particular mammalian cells is to try to increase the integral of viable cell concentration in the cultivation system, i.e. the integral from the viable cell concentration curve and the time curve, since the integral of viable cell concentration has positive correlation with product concentration, for example with the polypeptide concentration (Renard, J. M., et al., Biotechnology Letters, 1988, 10(2): 91-96). The integral of viable cell concentration can be increased either by increasing the viable cell concentration or by lengthening the process time.

The process time can be prolonged if the cells remain alive for a long time in the bioreactor, i.e. if the vitality of the cells remains high for a long time, or alternatively if the stationary phase is lengthened. If the vitality is low, there are many dead cells in the culture, which undergo lysis during fermentation and release cell-specific proteins. In its turn, a higher total specific-protein content in the culture makes purification of the desired polypeptide more difficult. There are several explanations for the decrease in vitality and hence short process time: in a nutrient medium, in particular in a cell culture medium, a substrate may have a limiting effect, the cells may enter into apoptosis because of the physical fermentation conditions, or byproducts of metabolism may accumulate in the medium, and exert a toxic action on the cells.

It would be desirable to have a nutrient medium or a method in which cell vitality remains high for a long time, i.e. in which the stationary phase is lengthened, as the highest viable cell concentration is already attained in the stationary phase. Lengthening of the stationary phase leads to an increase of the integral of viable cell concentration and to increased product formation. Another parameter for increasing the integral of viable cell concentration is an increase in the peak cell density. The peak cell density can be increased further by means of better nutrient media and better methods of cultivation.

The peak cell density or cell vitality is a function of the cell metabolism. If the cells have an inefficient metabolism, they excrete energy-rich intermediate metabolites, such as lactate, into the medium. Cells can also excrete toxic intermediate metabolites into the medium, such as ammonium. In its turn, ammonium can adversely affect cell growth, productivity and product quality, for example glycosylation. For example, when cells with high glycolytic activity metabolize glucose, there is a shift in the intracellular concentration of the glycolytic intermediates. This can affect the expression profile of various genes that are necessary for stress stability, productivity and growth (Verstrepen, K. J., et al., Trends Biotechnol., 2004, 22 (10): 531-537). In such conditions the integral of viable cell concentration is low, with consequent reduced product formation.

Compared with primary cells, permanent cell lines are known to have a degenerated cell metabolism. In this connection, a number of enzymes of primary metabolism were compared between cell lines and primary cells. No activity of enzymes that link glycolysis with the citrate cycle could be detected in the cell lines tested, whereas they were present in primary cells (Neerman, J. and Wagner, R., J. Cell. Physiol., 1996, 166 (1): 152-169). In many continuous mammalian cells the flux from glucose to lactate is high, whereas the flux from pyruvate to the citrate cycle is low. Glucose is largely converted to lactate by the cells and then the energy-rich lactate is excreted into the nutrient medium, in particular into a cell culture medium. Apart from glucose, the cell lines metabolize glutamine at a high rate as an energy source. Therefore both substrates, glucose and glutamine, are among the most important substrates in nutrient media for continuous mammalian cells.

There have been several attempts to improve the cell metabolism of permanent cell lines. Limiting the glucose and glutamine in the process was tried as a means of restricting the glycolytic flux. Substrate restriction was presumed to suppress the overflow metabolism of the cells, so that the cells would produce less lactate and ammonium (US 2004/0048368 A1; Europa, A. F., et al., Biotechnol. Bioeng., 2000, 67(1): 25-34). The effect of glutamine restriction on the growth and apoptosis of CHO cells was investigated closely. It was shown that with glutamine restriction the cell growth rate decreases, but the proportion of cells entering apoptosis is lower (Sanfeliu, A. and Stephanopoulus, G., Biotechnol. and Bioeng., 1999, 64(1): 46-53). In WO 98/41611 it was proposed to regulate the glucose and glutamine concentration to a low value. This should take place through coupling of the glucose or glutamine concentration with the oxygen consumption rate. A prerequisite for this procedure is complex regulation and replenishment of the substrates, so that the process is difficult to control, especially in large-scale conditions. The risk of a fermenter breakdown and the associated financial risk is high. On the other hand EP 0435911 B1 teaches that inter alia glutamine must be increased in standard cell culture media in order to achieve improved cell growth and increased product formation. Similarly, the replenishment of animal cells with glutamine is considered to be necessary in fed-batch or in perfusion for the production of biopharmaceuticals (Duvar, S. et al., Transkript, 2004, 5(1): 34-36). Thus, there are contradictory statements in the literature concerning the role of glutamine with respect to cell metabolism.

Chen, K., et al. (Biotechnol. Bioeng., 2001, 72: 55-62) tried to suppress lactate formation by homologous recombination. A copy of the lactate dehydrogenase gene was inactivated and consequently the cell-specific lactate formation rate was reduced by 50%. Irani, N., et al. (J. Biotechnol., 1999, 66: 238-246) cloned the pyruvate carboxylase gene into a cell line. The expectation was that the cells would then deliver more pyruvate into the citrate cycle and therefore produce less lactate. According to EP 0 338 841 A1 the glutamine synthetase gene was cloned in cells as a selection marker. This had the advantage that no external glutamine had to be added to the nutrient medium. Cells produced glutamine themselves and excreted little ammonium.

Altamirano, C. et al. (Biotechnol. Progress, 2000, 16(1): 69-75) replaced glucose and glutamine with alternatives that are difficult to metabolize, in this case with galactose and glutamate, in a low-protein medium in batch conditions. As a result, the cells did indeed produce less metabolic byproducts, but both cell growth and product formation were lower than in the control. Development of a two-phase process was also proposed: cells should grow in glucose initially, and then utilize galactose as source of carbohydrate in the production phase (Altamirano, C., et al., Biotechnol. Bioeng., 2001, 76(4): 351-60; Altamirano, C., et al., J. Biotechnology, 2004, 110(2): 171-9).

U.S. Pat. No. 4,049,494 describes a serum-free, chemically defined and autoclavable nutrient medium. The medium possesses the property that it is glutamine-free and at the same time contains glucose and pyruvate. The medium was specially developed for virus production with baby hamster kidney cells. Similarly, WO 03/106661 A2 describes a substrate combination for the cultivation of mammalian cells. The combination comprises a glutamine-free and at the same time pyruvate-containing nutrient medium. This substrate combination is said to reduce the formation of lactate and/or ammonium. It was shown that a combination of 1 mM pyruvate with 5.5 mM glucose in a nutrient medium promotes the maturation of cumulus-cell-enclosed mouse oocytes. Interestingly, little if any effect of glutamine on the maturation of the cells could be demonstrated (Downs, S. M. and Hudson, E. D., Zygote, 2000, 8(4): 339-51). Hassel, T. and Butler, M. (J. Cell Science, 1990, 96 (Pt3): 501-8) replaced glutamine with glutamate or 2-oxoglutarate in a nutrient medium and adapted cells to this medium. After the adaptation phase the McCoy cells used produced less lactate and ammonium. It must be emphasized that in this instance the cells grew on microcarriers and were either in the later exponential growth phase or in the stationary phase. The cells have an altered metabolic profile in these growth phases. In addition, pre-adaptation of the cells to glutamine-free medium was necessary.

In a special nutrient medium, glutamine was removed from the nutrient medium. Without cell adaptation, the clone under investigation simply grew in the special nutrient medium. As a result ammonium formation was reduced and product formation was increased (Deer, F., and Cunningham, M., Genetic Eng. News, 2000, 20(7): 42). Kurano, N., et al., 1990 (Journal of Biotechnology, 15(1-2): 113-28) replaced glutamine with asparagine. A CHO culture was supplemented with asparagine in fed-batch conditions and in glutamine-free conditions and ammonium formation was reduced.

In addition, glutamine was replaced in nutrient media with dipeptides, alanyl-glutamine (Ala-Gln) or glycyl-glutamine (Gly-Gln). It was shown that owing to this strategy the cells produced less ammonium (Roth, E. et al., In vitro cellular & developmental biology, 1988, 24(7): 696-698; Christie, A. and Butler, M., J. Biotechnology, 1994, 37(3):277-90). Glutamine was replaced with the stable glutamine alternative L-alanyl-glutamine (Glutamax) in order to investigate the effect of glutamine restriction with this substance (Sanfeliu, A. and Stephanopoulus, G., Biotechnol. and Bioeng., 1999, 64(1): 46-53).

Another combination of substances that is said to reduce glucose consumption and lactate formation was disclosed in EP 1 342 780 A1. According to this, free unbound citrate in combination with iron citrate bound in a complexing agent is to be added to the nutrient medium.

In a nutrient medium (perfusate), lactate and pyruvate in 10:1 ratio were supplied as substrate to rat heart cells. Lactate was used because lactate is a preferred substrate of the heart cells. It was shown that the glycolytic flux had been inhibited through addition of lactate (Depre, C. et al., Acta Cardiologica, 1993, 48(1): 147-64; Ovchinnikov, I. V. and Kim, N. P., Ukrainskii Biokhimicheskii Zhurnal, 1985, 57(4): 72-5).

The action of succinate, malate, lactate and pyruvate on hamster embryos was investigated in a chemically defined, protein-free medium. It was shown that succinate and malate in the nutrient medium support the development of blastocytes (Ain, R. and Seshagiri, P. B., Molecular Reproduction & Development, 1997, 47(4): 440-7). In this work the focus was on developmental biology, in particular the development of blastocytes (primary cells).

It was reported that the CHO (Chinese hamster ovary) cells are not able to utilize ribose, lactose, sucrose, glycerol, lactate, pyruvate, citrate, succinate, fumarate or malate as energy source (Faik, P. and Morgan, M. J., Cell Biol. Int. Reports, 1977, 1(6): 555-62). It was found, surprisingly, that precisely these substances can be utilized by cells, in particular by CHO cells, as substrate if, according to the invention, the correct concentration is selected and moreover the correct concentration of amino acid (glutamine, glutamate, asparagine) and source of carbohydrate are selected.

Acetate was added to the nutrient medium on the basis that it increases productivity performance of the cells in a comparable manner to butyrate (WO 03/064630). Glucose was combined with another C2-carbon source so as to be able to select a genetically altered yeast strain (WO 2004/099425). In this work, however, the focus is on a method for selecting a new yeast strain, not for the cultivation of an organism.

SUMMARY OF THE INVENTION

The technical problem forming the basis of the invention is the provision of an improved-yield nutrient medium, in particular a cell culture medium, a cell culture and a method for the cultivation of cells or cell cultures, in particular for the production of biological products from cells or cell cultures, in which the integral of viable cell concentration of a cell culture is increased, and accordingly a larger amount of desirable biological product can be obtained for the entire duration of the process. It is also further desirable that the nutrient medium, in particular the cell culture medium, can be used for cells that have one or more possibly even not precisely localized metabolic blockades in the glycosylation pathway or in the energy metabolism pathway in particular in the citrate cycle or glycolysis or have a blockade in the transport of metabolites from the medium into the cell, and/or inside the cell between the organelles.

The invention is therefore also based on the technical problem of providing a nutrient medium for the cultivation of cells or cell cultures, also of cells with metabolic blockade in the glycosylation pathway or in the energy metabolism pathway, e.g. in the citrate cycle or glycolysis, or of cells that have a blockade in the transport of metabolites from the medium into the cell, and/or inside the cell between the organelles, in which cell growth is improved, or the formation of metabolic byproducts is reduced, and accordingly a larger amount of desirable biological product can be obtained for the entire duration of the process.

The invention is also based on the technical problem of providing methods of selection of special cells, in particular genetically modified and/or metabolically altered, in particular optimized, cells.

It was found, surprisingly, that the addition of organic acids or salts, derivatives or complexes of organic acids, selected from the group comprising citric acid, succinic acid, malic acid, α-keto-glutaric acid, fumaric acid, oxalacetic acid, isocitric acid, oxalosuccinic acid, tartaric acid, adipic acid, lactic acid to a nutrient medium, in particular to a cell culture medium, increased the growth and/or the productivity of the cells and/or reduced the formation of toxic metabolites. Organic acids or salts or complexes of organic acids, selected from the group comprising succinic acid, malic acid, α-keto-glutaric acid, fumaric acid, oxalacetic acid, isocitric acid, oxalosuccinic acid, tartaric acid, adipic acid, and lactic acid, are preferred according to the invention.

The increase in productivity and/or decrease in formation of byproducts produced according to this aspect of the invention can be achieved if the substances according to the invention are added on their own to a nutrient medium, in particular a cell culture medium, or are combined with one another, or are combined with carbohydrates, or without carbohydrates, are added in the medium, in particular if the substances are added to a medium that contains glutamine, or does not contain glutamine, or are used in a medium that contains glutamine substitutes, or does not contain glutamine substitutes, or has a high asparagine concentration, or contains asparagine substitutes, or has a high glutamate concentration, or contains glutamate substitutes.

DETAILED DESCRIPTION OF CERTAIN EMBODIMENTS OF THE INVENTION

The invention solves the technical problem on which it is based, in particular by providing a nutrient medium, in particular a cell culture medium, a cell culture and a method according to the patent claims.

In particular the invention solves the technical problem on which it is based by providing a nutrient medium, in particular a cell culture medium, for the cultivation of a cell culture, comprising at least one cell, where the nutrient medium, in particular the cell culture medium, contains at least one substance selected from the group comprising citric acid, succinic acid, malic acid, α-keto-glutaric acid, fumaric acid, oxalacetic acid, isocitric acid, oxalosuccinic acid, tartaric acid, adipic acid, lactic acid and mixtures thereof and salts, derivatives or complexes of these acids. According to the invention, the nutrient medium, in particular the cell culture medium, preferably contains at least one substance selected from the group comprising succinic acid, malic acid, α-keto-glutaric acid, fumaric acid, oxalacetic acid, isocitric acid, oxalosuccinic acid, tartaric acid, adipic acid, lactic acid and mixtures thereof and salts or complexes of these acids.

"Salts of the acids used according to the invention" means in particular succinate, malate, α-keto-glutarate, fumarate, oxalacetate, isocitrate, oxalosuccinate, tartrate, adipate, or lactate. "Salt of citric acid" means citrate.

The nutrient medium according to the invention, in particular the cell culture medium, preferably contains at least two substances selected from the group comprising succinic acid, malic acid, α-keto-glutaric acid, fumaric acid, oxalacetic acid, isocitric acid, oxalosuccinic acid, tartaric acid, adipic acid, lactic acid and mixtures thereof and salts or complexes of these acids, and one or more of the aforementioned acids can also be in the form of a salt or complex. Especially preferably, the group is expanded to include citric acid.

Preferably the nutrient medium contains lactic acid. Preferably the nutrient medium contains lactate. Preferably the nutrient medium contains at least one lactic acid complex. Preferably the nutrient medium contains a lactic acid derivative.

Preferably the nutrient medium contains, as lactic acid derivative, alanine and/or at least one alanine-containing peptide. Preferably the nutrient medium contains alanine and/or at least one alanine-containing peptide at a concentration of 0.1 g/l or higher, especially preferably 1 g/l or higher, more preferably 5 g/l or higher, most preferably 25 g/l or higher. Preferably the nutrient medium contains, as lactic acid derivative, pyruvate and/or at least one pyruvate derivative. Preferably the nutrient medium contains pyruvate and/or at least one pyruvate derivative at a concentration of 0.1 g/l or higher, especially preferably 1 g/l or higher, most preferably 5 g/l or higher, most preferably 25 g/l or higher.

In a preferred embodiment the concentrations stated in the description are final concentrations. In a preferred embodiment the concentrations stated in the description are total concentrations of the respective substances.

Preferably the nutrient medium contains lactic acid, lactate, at least one lactic acid complex and/or at least one lactic acid derivative at a concentration of 0.1 g/l or higher, preferably 1 g/l or higher, especially preferably 5 g/l or higher, more preferably 25 g/l or higher.

Preferably the nutrient medium contains succinic acid. Preferably the nutrient medium contains succinate. Preferably the nutrient medium contains a succinic acid derivative. Preferably the nutrient medium contains a succinate derivative.

In a preferred embodiment of the present invention the nutrient medium, in particular the cell culture medium, according to the invention has all the stated acids or substances, and instead of the acids it is also possible to use the corresponding salts or complexes. In particular in such a composition it is possible to cultivate metabolically blocked cells, in particular when the site of the block, e.g. in the glycosylation pathway or in the energy metabolism pathway, for example in the citrate cycle or glycolysis, cannot be localized exactly or cells have a blockade in the transport of metabolites from the medium into the cell, and/or inside the cell between the organelles. Preferably the nutrient medium, in particular the cell culture medium, thus contains succinic acid, malic acid, α-keto-glutaric acid, fumaric acid, oxalacetic acid, isocitric acid, oxalosuccinic acid, tartaric acid, adipic acid and lactic acid, and one or more of the aforementioned acids can also be in the form of salt or complex. Especially preferably, the group is expanded to include citric acid. The substances according to the invention are suitable for the long-lasting cultivation of organisms, especially for the cultivation of animal cells, in particular for the cultivation of mammalian cells.

Preferably the nutrient medium according to the invention, in particular the cell culture medium according to the invention, contains the at least one substance according to the invention at a concentration of at least 15 mg/l, more preferably at least 30 mg/l, especially preferably at least 100 mg/l, in particular at least 300 mg/l, most preferably at least 1000 mg/l. Preferably the nutrient medium according to the invention, in particular the cell culture medium according to the invention, contains the at least one substance according to the invention at a concentration of 0.03 g/l or higher, more preferably 0.1 g/l or higher, especially preferably 1 g/l or higher, in particular 5 g/l or higher, most preferably 25 g/l or higher. In a further preferred embodiment the nutrient medium according to the invention is a feed medium. Preferably the nutrient medium according to the invention, in particular feed medium, contains the at least one substance according to the invention at a concentration of 0.2 g/l or higher, more preferably 1 g/l or higher, especially preferably 5 g/l or higher, very preferably 25 g/l or higher, most preferably at least 100 g/l.

In a preferred embodiment the nutrient medium according to the invention, in particular the cell culture medium according to the invention, contains at least one carbohydrate, especially preferably a monosaccharide or a disaccharide. Preferably the nutrient medium contains one carbohydrate. Preferably the carbohydrate is selected from the group comprising glucose, galactose, fructose, mannose, ribose, glucosamine, sucrose, lactose and mixtures thereof.

Preferably the nutrient medium contains the at least one carbohydrate at a concentration of 0.1 g/l or higher, more preferably 1 g/l or higher, especially preferably 5 g/l or higher, most preferably 25 g/l or higher, most preferably 100 g/l or higher.

Preferably the nutrient medium contains galactose. Preferably the nutrient medium contains galactose and a second carbohydrate. Preferably the nutrient medium contains galactose at a concentration of 0.1 g/l or higher, more preferably 1 g/l or higher, especially preferably 5 g/l or higher, most preferably 25 g/l or higher, most preferably 100 g/l or higher.

Preferably the nutrient medium contains glucose at a concentration of 100 g/l or lower, more preferably 25 g/l or lower, more preferably 5 g/l or lower, especially preferably 1 g/l or lower, most preferably 0.1 g/l or lower. Preferably the nutrient medium is glucose-free.

In a further preferred embodiment the nutrient medium according to the invention, in particular the cell culture medium according to the invention, is free from carbohydrates.

Preferably the nutrient medium according to the invention, in particular the cell culture medium according to the invention, contains glutamine at a concentration of less than 8 mmol/l, preferably less than 5 mmol/l, especially preferably less than 3 mmol/l, most preferably less than 2 mmol/l. However, the nutrient medium, in particular the cell culture medium, can also preferably be glutamine-free.

In a further preferred variant the nutrient medium according to the invention, in particular the cell culture medium according to the invention, contains at least one glutamine derivative, thus at least one glutamine-containing glutamine substitute, especially preferably a glutamine-containing dipeptide. Preferably the at least one glutamine derivative is a glutamine-containing peptide.

Preferably the nutrient medium according to the invention, in particular the cell culture medium according to the invention, contains glutamine derivatives at a total concentration of more than 30 mg/l, preferably more than 150 mg/l, especially preferably more than 750 mg/l, most preferably more than 2000 mg/l. Preferably the nutrient medium according to the invention, in particular the cell culture medium according to the invention, contains glutamine derivatives at a concentration of 0.05 g/l or higher, preferably 0.2 g/l or higher, especially preferably 0.8 g/l or higher, most preferably 3.2 g/l or higher. However, in a preferred variant the nutrient medium, in particular the cell culture medium, can also be free from glutamine derivatives.

Preferably the nutrient medium contains asparagine. Preferably the nutrient medium contains at least one asparagine substitute, in particular at least one asparagine derivative. Preferably the nutrient medium according to the invention, in particular the cell culture medium according to the invention, contains asparagine or at least one asparagine substitute, especially preferably at least one asparagine derivative, at a high concentration, i.e. at a concentration, in particular total concentration, of more than 0.05 g/l, especially preferably more than 0.15 g/l, more preferably more than 0.3 g/l, and in particular more than 0.6 g/l Preferably the nutrient medium according to the invention, in particular the cell culture medium according to the invention, contains glutamate or at least one glutamate substitute, preferably at least one glutamate derivative, at a high concentration, i.e. at a concentration of 0.05 g/l or higher, more preferably 0.15 g/l or higher, most preferably 0.3 g/l or higher, in particular 0.6 g/l or higher.

In an especially preferred embodiment the present invention relates to a cell culture medium that contains lactic acid and galactose and the aforementioned high asparagine concentration, but at the same time is glutamine-free.

In a further preferred embodiment the present invention relates to a cell culture medium, which contains lactic acid, galactose and asparagine at the aforementioned high concentration and at the same time is glutamine-free, but has at least one glutamine-containing peptide.

In a further preferred embodiment the present invention relates to a cell culture medium which has lactic acid and galactose, and furthermore has a high glutamate concentration at the aforementioned concentration, but at the same time is glutamine-free.

In a further preferred embodiment the present invention relates to a cell culture medium which has succinic acid and a high concentration of asparagine or asparagine substitute of the aforementioned concentrations, but at the same time is glutamine-free.

According to the invention the nutrient medium is preferably glucose-free and glutamine-free and contains asparagine at a concentration of 0.05 g/l or higher, more preferably 0.15 g/l or higher, especially preferably 0.3 g/l or higher, most preferably 0.6 g/l or higher, and lactic acid and galactose. According to the invention the nutrient medium is preferably glucose-free and glutamine-free and contains glutamate at a concentration of 0.05 g/l or higher, more preferably 0.15 g/l or higher, especially preferably 0.3 g/l or higher, most preferably 0.6 g/l or higher, and lactic acid and galactose. According to the invention the nutrient medium is preferably glucose-free and contains glutamine-containing peptides, lactic acid and galactose.

In a further preferred embodiment the nutrient medium according to the invention, in particular the cell culture medium according to the invention, is a feed medium.

Preferably the feed medium contains lactic acid, lactate, at least one lactic acid complex and/or at least one lactic acid derivative at a concentration of 1 g/l or higher, preferably 5 g/l or higher, especially preferably 25 g/l or higher, most preferably 100 g/l or higher.

Preferably the feed medium contains galactose at a concentration of 1 g/l or higher, especially preferably 5 g/l or higher, most preferably 25 g/l or higher, most preferably 100 g/l or higher.

Preferably the nutrient medium according to the invention, especially preferably feed medium, contains glutamine derivatives at a concentration of 0.2 g/l or higher, more preferably 1 g/l or higher, especially preferably 5 g/l or higher, most preferably 10 g/l or higher.

Preferably the nutrient medium according to the invention, in particular the feed medium, contains asparagine or at least one asparagine substitute, especially preferably at least one asparagine derivative, at a concentration of 0.2 g/l or higher, more preferably 1 g/l or higher, especially preferably 2 g/l or higher, in particular 5 g/l or higher, most preferably 10 g/l or higher.

Preferably the feed medium according to the invention contains glutamate or at least one glutamate substitute, especially preferably at least one glutamate derivative, at a concentration of 0.2 g/l or higher, preferably 1 g/l or higher, especially preferably 2 g/l or higher, in particular 5 g/l or higher, most preferably 10 g/l or higher.

In a preferred variant the nutrient medium according to the invention, in particular the cell culture medium according to the invention, is a basal medium, preferably a basal medium with an osmolality of 240 to 360 mOsmol/kg $H_2O$. In a preferred variant the nutrient medium according to the invention, in particular the cell culture medium according to the invention, is a basal medium, more preferably a basal medium with an osmolality of 280 to 350 mOsmol/kg $H_2O$, most preferably a basal medium with an osmolality of 280 to 320 mOsmol/kg $H_2O$.

In a further preferred variant the nutrient medium according to the invention, in particular the cell culture medium according to the invention, is a feed medium, preferably a feed medium with an osmolality of 150 to 1500 mOsmol/kg $H_2O$.

According to the invention, the nutrient medium is preferably serum-free. According to the invention, the nutrient medium preferably contains serum.

A nutrient medium is in particular a cell culture medium. According to the invention, the nutrient medium is preferably a liquid nutrient medium, in particular a liquid cell culture medium.

For a person skilled in the art, the concentration ranges of the ingredients that are to be selected, thus also the maximum concentrations of the ingredients that are to be selected, can be determined without special effort from the stated preferred minimum figures for the concentration of the stated ingredients in the nutrient medium. According to the invention, the concentration of an organic acid used according to the invention is preferably at most 200 g/l, especially preferably 100 g/l, more preferably 50 g/l, most preferably 25 g/l. According to the invention, the concentration of lactate and/or of a lactic acid derivative, in particular alanine and/or pyruvate, that is to be used according to the invention is preferably at most 200 g/l, especially preferably 100 g/l, in particular 50 g/l, most preferably 25 g/l. According to the invention, the concentration of a glutamine derivative that is to be used according to the invention is preferably at most 60 g/l, especially preferably 30 g/l, more preferably 10 g/l, very preferably 5 g/l, in particular 1.2 g/l, most preferably 1.1 g/l. According to the invention, the concentration of asparagine or of an asparagine derivative that is to be used according to the invention is preferably at most 60 g/l, especially preferably 30 g/l, more preferably 5 g/l, in particular 1.2 g/l, most preferably 1.1 g/l. According to the invention, the concentration of glutamate or of a glutamate derivative that is to be used according to the invention is preferably at most 60 g/l, especially preferably 30 g/l, more preferably 5 g/l, in particular 1.2 g/l, most preferably 1.1 g/l. According to the invention, the concentration of galactose that is to be used according to the invention is preferably at most 200 g/l, especially preferably 100 g/l, in particular 50 g/l, most preferably 25 g/l.

The invention also relates to the use of a nutrient medium according to the invention, in particular of a cell culture medium according to the invention, for the cultivation of a cell culture, comprising at least one cell.

The invention also solves the technical problem on which it is based by providing a cell or a cell culture. The cell or cell culture is, according to the invention, preferably optimized metabolically to such an extent that it can be cultivated in culture media and methods according to the invention.

According to the invention, the cell or cell culture is preferably characterized in that the cell culture can survive or can divide in a medium with substances according to the invention or the peak cell density is higher, or the stationary phase is longer, or the death phase is slower, or the formation of cell-metabolism byproducts, for example ammonium or lactate, is reduced.

According to the invention, a cell or cell culture is preferred which can metabolize lactic acid, and salts (lactate) or complexes of lactic acid, or salts of lactic acid substitutes. According to the invention, a cell or cell culture is preferred which can survive, and can preferably divide, in a glucose-free and glutamine-free medium, especially preferably can reach a higher integral of viable cells (IVC), most preferably produces less metabolic byproducts, in particular lactate or ammonium. According to the invention, a cell or cell culture is preferred which can survive, and preferably can divide, in a glucose-free medium, especially preferably can reach a higher integral of viable cells (IVC), most preferably produces less metabolic byproducts, in particular lactate or ammonium. According to the invention, a cell or cell culture is preferred which can survive, and can metabolize lactate, and preferably can divide in a glucose-free and glutamine-free medium, especially preferably can reach a higher integral of viable cells (IVC), most preferably produces less metabolic byproducts, in particular lactate or ammonium. According to the invention, a cell or cell culture is preferred which can survive, and can metabolize lactate and has a high asparagine consumption in a glucose-free and glutamine-free medium, preferably can divide in such a medium, especially preferably can reach a higher integral of viable cells (IVC), most preferably produces less metabolic byproducts, in particular lactate or ammonium. According to the invention, a cell or cell culture is preferred which can survive, and can metabolize lactate and has a high glutamate consumption in a glucose-free and glutamine-free medium, preferably can divide in such a medium, especially preferably can reach a higher integral of viable cells (IVC), most preferably produces less metabolic byproducts, in particular lactate or ammonium. According to the invention, a cell or cell culture is preferred which can survive, and can metabolize lactate and can metabolize galactose in a glucose-free and glutamine-free medium, preferably can divide in such a medium, especially preferably can reach a higher integral of viable cells (IVC), and most preferably produces less metabolic byproducts, in particular lactate or ammonium. According to the invention, a cell or cell culture is preferred which can survive, and can metabolize lactate and can metabolize galactose in a glucose-free and glutamine-free medium, and has a high asparagine consumption or a high glutamate consumption, preferably can divide in such a medium, especially preferably can reach a higher integral of viable cells (IVC), and most preferably produces less metabolic byproducts, in particular lactate or ammonium.

The invention also solves the technical problem on which it is based by providing a method for the cultivation of a cell culture, comprising at least one cell, in which the cell culture is put in a nutrient medium and is cultivated and in which the pH value of the nutrient medium during at least one fifth of the cultivation time is pH 7.2 or more basic.

The invention also solves the technical problem on which it is based by providing a method for the cultivation of a cell culture, comprising at least one cell, in which the cell culture is put in a nutrient medium according to the invention, in particular in a cell culture medium according to the invention, and is cultivated.

The cell culture, comprising at least one cell, that is put in the nutrient medium according to the invention, in particular in the cell culture medium according to the invention, is preferably used for the production of a biological product.

The biological product is preferably selected from at least one polypeptide, at least one protein, at least one virus component, at least one virus or from a mixture thereof. Especially preferably the biological product is at least one vaccine.

The biological product is preferably obtained from the cell culture and/or from the nutrient medium, in particular from the cell culture medium according to the invention.

Preferably the at least one cell contains at least one gene, which encodes the biological product.

According to the invention, cell culture means at least one cell, which is kept alive in a medium, preferably a nutrient medium, in particular a cell culture medium, and preferably also divides in the medium or is induced to undergo cell division. According to the invention, the at least one cell is preferably a eukaryotic cell, especially preferably a fungal cell, in particular a yeast cell, a plant cell or an animal cell, for example an insect cell or mammalian cell, in particular a human or rodent cell, a hamster cell or a myeloma cell, for example a CHO, NSO, PERC6, HEK293 or BHK21 cell. According to the invention, the at least one cell is also preferably a prokaryotic cell. According to the invention, the at least one cell is also preferably a descendant of one of the aforementioned cells.

According to the invention, the at least one cell preferably originates from a cell line, in particular from an immortalized cell line and/or from a tumor cell line. According to the invention, the at least one cell is also preferably a primary cell. Examples of cells according to the invention are presented hereafter.

The cell culture is, according to the invention, preferably a cell population. Alternatively, the cell culture is, according to the invention, preferably a cell clone. The cell culture can according to the invention also comprise several cell types or cell species, preferably the cell culture can consist of or comprise several cell types or cell species. The cell culture can preferably, according to the invention, consist of unions of cells or comprise unions of cells.

According to the invention, the method according to the invention is preferably a batch method, a split-batch method, a fed-batch method, a continuous method or a perfusion method.

Preferably, according to the invention, the pH value of the nutrient medium at the end of cultivation is 7.2 or more basic, more preferably 7.3 or more basic, especially preferably 7.4 or more basic, most preferably 7.5 or more basic, quite especially preferably 7.6 or more basic, most preferably 7.7 or more basic.

Preferably, according to the invention, the pH value of the nutrient medium during at least one fifth, more preferably during at least two fifths, most preferably during at least three fifths, in particular during at least four fifths, of the cultivation time is pH 7.2 or more basic, more preferably 7.3 or more basic, especially preferably 7.4 or more basic, most preferably 7.5 or more basic, quite especially preferably 7.6 or more basic, most preferably 7.7 or more basic.

Preferably, according to the invention, the pH value of the nutrient medium during the cultivation process is pH 7.2 or more basic, more preferably 7.3 or more basic, especially preferably 7.4 or more basic, especially preferably 7.5 or more basic, quite especially preferably 7.6 or more basic, most preferably 7.7 or more basic.

Preferably, according to the invention, the pH value of the nutrient medium during the cultivation process is at least pH 6.6 and at most pH 7.9, more preferably at least pH 6.7 and at most pH 7.9, most preferably at least pH 6.8 and at most pH 7.9. Preferably, according to the invention, the pH value of the nutrient medium during the cultivation process is at least pH 6.6 and at most 7.5, more preferably at least pH 6.7 and at most pH 7.5, most preferably at least pH 6.8 and at most pH 7.5. Preferably, according to the invention, the pH value of the nutrient medium during the cultivation process is at least pH 6.6 and at most pH 7.2, more preferably at least pH 6.7 and at most pH 7.2, most preferably at least pH 6.8 and at most pH 7.2.

Preferably, according to the invention, the pH value of the nutrient medium during the cultivation process is never higher than pH 9.0, very preferably never higher than pH 8.5, more preferably never higher than pH 8.0, especially preferably never higher than pH 7.8, most preferably never higher than pH 7.7.

Preferably, according to the invention, the pH value during the cultivation process of the method according to the invention is more basic than pH 7.2, more preferably more basic than pH 7.3, more preferably more basic than pH 7.4, more preferably more basic than pH 7.5, especially preferably more basic than pH 7.6, most preferably more basic than pH 7.7. Preferably, according to the invention, the pH value during the cultivation process of the method according to the invention in at least four fifths (⅘) of the total cultivation time of the method according to the invention is more basic than pH 7.2, preferably more basic than pH 7.3, more preferably more basic than pH 7.4, more preferably more basic than pH 7.5, especially preferably more basic than pH 7.6, most preferably more basic than pH 7.7. The total cultivation time of the method according to the invention starts when a culture vessel is inoculated with cells in the production stage. Thus, the intermediate stages of cell cultivation for expanding cells for the production stage do not count towards the total cultivation time.

Preferably, according to the invention, the pH value at the end of the cultivation process of the method according to the invention is more basic than pH 7.2, preferably more basic than pH 7.3, more preferably more basic than pH 7.4, more preferably more basic than pH 7.5, especially preferably more basic than pH 7.6, most preferably more basic than pH 7.7. Preferably, according to the invention, the pH value of the method according to the invention is at most 7.8, more preferably at most 8.0.

The invention also relates to a method of production of a nutrient medium according to the invention, in particular of a cell culture medium according to the invention, wherein at least one substance selected from the group comprising citric acid, succinic acid, malic acid, α-keto-glutaric acid, fumaric acid, oxalacetic acid, isocitric acid, oxalosuccinic acid, tartaric acid, adipic acid, lactic acid and mixtures thereof and salts, derivatives or complexes of these acids, is dissolved in water or a cell culture solvent or nutrient medium solvent, in particular a cell culture medium solvent, or a conventional nutrient medium, in particular cell culture medium.

The invention also relates to a method of production of a nutrient medium according to the invention, in particular of a cell culture medium according to the invention, wherein at least one substance selected from the group comprising citric acid, succinic acid, malic acid, α-keto-glutaric acid, fumaric acid, oxalacetic acid, isocitric acid, oxalosuccinic acid, tartaric acid, adipic acid, lactic acid and mixtures thereof and salts or complexes of these acids, is dissolved in water or a cell culture solvent or nutrient medium solvent, in particular a cell culture medium solvent, or a conventional nutrient medium, in particular cell culture medium.

The invention also relates to a method, in particular a method according to the invention for the cultivation of a cell culture, for the selection of a genetically modified, in particular metabolically optimized, cell from a cell population, wherein a) a cell culture is cultivated as a cell population in a nutrient medium according to the invention for at least one week, especially preferably is cultivated for at least four weeks; and then b) the cell is isolated. The isolated cell is a living cell. According to the invention, the cultivation preferably takes place according to a method of cultivation according to the invention.

It was found, surprisingly, that during cultivation in a nutrient medium according to the invention, novel cells can be selected and isolated, which are genetically modified. The genetic modification is manifested for example by a change, in particular an improvement of cell metabolism. In particular, said cells with the altered cell metabolism grow especially well, or anyway, in a medium according to the invention, in comparison with conventional cells. The altered cell metabolism arises through genetic modifications. Therefore by cultivating cell populations in a nutrient medium according to the invention it is possible to isolate said genetically modified cells.

Preferably, according to the invention, the at least one cell isolated in step b) is transferred to a new culture medium in an additional step c). Especially preferably, according to the invention, the new nutrient medium is a fresh nutrient medium. Especially preferably, according to the invention, the new nutrient medium is a nutrient medium according to the invention. Especially preferably, according to the invention, the new nutrient medium is not a nutrient medium according to the invention, i.e. it is a nutrient medium from the state of the art. Preferably, according to the invention, the at least one cell isolated in step b) is expanded in step c).

Preferably, according to the invention, the nutrient medium when carrying out the method according to the invention has a pH value more basic than 7.2, preferably more basic than pH 7.3, most preferably more basic than pH 7.4, more preferably more basic than pH 7.5, especially preferably more basic than pH 7.6, most preferably more basic than pH 7.7.

Preferably, according to the invention, when carrying out the method according to the invention, in at least four fifths (⅘) of the total cultivation time the nutrient medium has a pH value more basic than pH 7.2, preferably more basic than pH 7.3, more preferably more basic than pH 7.4, more preferably more basic than pH 7.5, especially preferably more basic than pH 7.6, most preferably more basic than pH 7.7. The total cultivation time of the method according to the invention starts when a culture vessel is inoculated with cells in the production stage. Thus, the intermediate stages of cell cultivation for expanding cells for the production stage does not count towards the total cultivation time.

Preferably, according to the invention, at the end of the cultivation process the nutrient medium has a pH value more basic than 7.2, preferably more basic than pH 7.3, more preferably more basic than pH 7.4, more preferably more basic than pH 7.5, especially preferably more basic than pH 7.6, most preferably more basic than pH 7.7. Preferably, according to the invention, the pH value is at most 7.8, more preferably at most 8.0.

Preferably, according to the invention, the at least one cell is subcultured for at least one passage, especially preferably for at least 2 passages, most preferably for at least 5 passages. Preferably, according to the invention, the at least one cell is subcultured until a split ratio of greater than 1 to 4 is reached.

The invention also relates to a selected cell, obtainable from a method according to the invention. Preferably, according to the invention, the cell can metabolize lactate as a source of carbon. Preferably, according to the invention, the cell has a split ratio of at least 1 to 4 with galactose as the sole source of carbon. Preferably, according to the invention, in a glucose-free and glutamine-free medium the cell has a split ratio of at least 1 to 4. Preferably, according to the invention, the growth rate (p) of the cell is less than 24 hours, especially preferably less than 20 hours, especially preferably less than 18 hours. The invention also relates to a cell culture that contains at least one cell according to the invention.

Preferably, according to the invention, the cell culture can metabolize lactate as a source of carbon. Preferably, according to the invention, the cell culture has a split ratio of at least 1 to 4 with galactose as the sole source of carbon. Preferably, according to the invention, in a glucose-free and glutamine-free medium the cell culture has a split ratio of at least 1 to 4. Preferably, according to the invention, the growth rate (p) of the cell culture thus isolated is less than 24 hours, especially preferably less than 20 hours, especially preferably less than 18 hours.

According to the invention, a method is also provided for obtaining a biological product from at least one cell, wherein the at least one cell is cultivated by a method according to the invention and the biological product is obtained therefrom.

The substances found according to this aspect of the invention are in particular succinic acid, malic acid, α-keto-glutaric acid, fumaric acid, oxalacetic acid, isocitric acid, oxalosuccinic acid, tartaric acid, adipic acid and lactic acid. According to the invention, these substances can also very preferably include citric acid.

The substances required according to this aspect of the invention can in particular be added individually to a nutrient medium, in particular to a cell culture medium, and preferably they are combined, i.e. singly or all together. However, combination with other carbohydrates is also preferred. Suitable carbohydrates are preferably selected from mono- and disaccharides such as glucose, galactose, glucosamine, fructose, ribose, mannose, sucrose, lactose. One or more of these carbohydrates can be selected as the source of carbohydrate.

The substances required according to this aspect of the invention can be used in a nutrient medium, in particular in a cell culture medium, that contains glutamine, or that is glutamine-free, or contains a low glutamine concentration, for example less than 8 mM, or the nutrient medium, in particular cell culture medium, can contain glutamine substitutes, for example alanyl-glutamine or glycyl-glutamine or the nutrient medium, in particular cell culture medium, can contain a mixture of several glutamine-containing peptides.

The substances required according to this aspect of the invention can preferably be used in a nutrient medium, in particular in a cell culture medium that contains asparagine or asparagine substitutes. The concentration of asparagine or of asparagine substitutes can preferably for example be higher than 0.05 g/l, more preferably higher than 0.15 g/l, especially preferably higher than 0.3 g/l, most preferably higher than 0.6 g/l. Asparagine substitutes can preferably be e.g. asparagine-containing peptides, for example, but not limited to this, Leu-Asn (Sigma, catalog number: L0641), or Ile-Asn (Sigma, catalog number: I3635), or Glu-Asn-Gly (Sigma, catalog number: P5148). The peptides can preferably basically contain 2 amino acids or more than 2 amino acids, in particular 3 or 4 amino acids.

The substances required according to this aspect of the invention can preferably be used in a nutrient medium, in particular in a cell culture medium that contains glutamate or glutamate substitutes. The concentration of glutamate or glutamate substitutes can preferably for example be higher than 0.05 g/l, more preferably higher than 0.15 g/l, especially preferably higher than 0.3 g/l, most preferably higher than 0.6 g/l. Glutamate substitutes can preferably be e.g. glutamate-containing peptides, for example but not limited to Asp-Glu (Sigma, catalog number: A1916-250MG), Glu-Glu (Sigma, catalog number: G3640-25MG), Glu-His (Sigma, catalog number: G6882-100MG), Glu-Leu (Sigma, catalog number: G7007-10MG), Glu-Lys (Sigma, catalog number: G5136-25MG). The peptides can preferably basically contain 2 amino acids or more than 2 amino acids, in particular 3 or 4 amino acids.

The invention also solves the problem on which it is based by providing a nutrient medium, a cell culture or a method for improving or extending the process time, the cell growth of a cell culture, comprising at least one cell, in an aqueous system, preferably, according to the invention, in a nutrient medium, in particular in a cell culture medium, wherein the cell growth is improved by adding the aforementioned substances, preferably in a nutrient medium, in particular in a cell culture medium. In particular the invention provides a nutrient medium, a cell culture and a method of achieving greater cell growth or of prolonging cell vitality or of reducing the formation of metabolic byproducts of a cell culture, comprising at least one cell, in an aqueous system, preferably, according to the invention, in a nutrient medium, in particular in a cell culture medium, with the cell growth being improved by adding organic acids in a nutrient medium, in particular in a cell culture medium.

According to the invention, the nutrient medium is characterized in that the nutrient medium preferably contains an organic acid or salts thereof. By adding the substances according to the invention, cell growth and/or product formation is increased, or the culture time is prolonged and/or the formation of metabolic byproducts is reduced.

According to the invention, the cell culture is characterized in that the cell culture can survive or divide in a medium with substances according to the invention or the peak cell density is increased, or the stationary phase is lengthened or the death phase is slower, or the formation of the byproducts of cell metabolism, for example ammonium or lactate, is reduced, wherein the medium can preferably contain a low glutamine concentration or no glutamine, and can contain a high asparagine concentration, can contain glucose or other carbohydrates, in particular is glucose-free or contains galactose. Instead of the high asparagine concentration, preferably a high glutamate concentration can also be contained.

Cell growth is according to the invention the growth of the cell culture, primarily but not exclusively caused by at least one cell division of at least one cell. If cell growth is increased, this is caused primarily by an increase in the frequency of cell division (cell growth rate, also called $\mu$).

The stationary phase of a cell culture is a typical growth phase of a growth curve of a cell culture, familiar to a person skilled in the art. This growth curve includes a lag phase, an exponential growth phase (log phase), a stationary phase and a death phase. The course of these phases can vary. The course and duration of these phases can also be influenced, for example by adding the substances according to the invention to a nutrient medium, in particular to a cell culture medium.

The "integral of viable cell concentration" means the viable cell concentration over a defined period of time (Renard, J. M., et al., Biotechnology Letters, 1988, 10(2): 91-96). The integral of viable cell concentration is thus in particular the number of all live cells for the duration of a process, in particular for the duration of cell cultivation. The integral of viable cell concentration can be altered either by the number of cells or by the duration of the process. Preferably, according to the invention, the integral of viable cell concentration is increased by a nutrient medium or method according to the invention.

Preferably, according to the invention, cell growth is improved or the peak cell density is increased, or the stationary phase is prolonged or the death phase is slowed down, or the formation of the byproducts of cell metabolism, for example ammonium or lactate, is reduced.

Preferably, according to the invention, the method according to the invention is a batch method, a split-batch method (repeated batch operation), a fed-batch method, a continuous method or a perfusion method.

Preferably, according to the invention, in a method according to the invention the cell culture, comprising at least one cell, is used for the production of a biological product. According to the invention, the biological product is preferably selected from at least one polypeptide, at least one protein, at least one virus component, at least one virus or from a mixture thereof. According to the invention, the biological product is preferably at least one vaccine.

For the production of a desired biotechnological product, in particular a polypeptide, protein or a vaccine, depending on the product either prokaryotic cells, for example bacteria, or eukaryotic cells, for example yeast cells or plant cells, but in particular animal cells, preferably mammalian cells, are used. The gene of the product to be produced can occur naturally or by recombinant means in the host cells. The product spectrum can vary from peptides with few amino acids to whole viruses. Especially in the case of complex proteins, which after translation are altered in a post-translational process, in particular are glycosylated, preferably animal cells are used. Another variant envisages the use of other eukaryotic cells, for example yeast.

According to the invention, the biological product is preferably obtained from the cell culture and/or from the cell culture supernatant, or from the cells themselves (intracellularly).

Preferably, according to the invention, the biological product can also be the cell itself, for example it can be a primary cell, a stem cell, a union of primary cells, a tissue constituent, or a complete tissue.

Preferably, according to the invention, the at least one cell contains at least one gene, which encodes the biological product. The gene can be a foreign gene, i.e. a gene that does not occur naturally in the production cell or the gene can be a cell-specific gene, which occurs naturally in the production cell. Said cell-specific gene can for example be present actively or inactively in the production cell. When the cell-specific gene was inactive, the gene could have been activated through external intervention.

According to the invention, a method is also provided for the cultivation of at least one cell as a cell culture, the at least one cell being cultivated in a nutrient medium, in particular in a cell culture medium, and preferably, according to the invention, its cell growth is stimulated by a method according to the invention.

According to the invention, a method is also provided for obtaining a biological product from at least one cell, the at least one cell being cultivated by a method according to the invention and the biological product is obtained therefrom.

It was found, surprisingly, that these particular organic acids (citric acid, succinic acid, malic acid, α-keto-glutaric acid, fumaric acid, oxalacetic acid, isocitric acid, oxalosuccinic acid, tartaric acid, adipic acid, lactic acid) promote cell growth and/or polypeptide production and/or suppress the formation of metabolic byproducts, especially when higher concentrations are used. In particular, when these components are used in a glutamine-free or low-glutamine nutrient medium, or are used in a medium with high asparagine concentration, or asparagine substitute concentration, or are used in a medium with high glutamate concentration, or with high glutamine substitute concentration, or are used in a medium with or without glucose, or are used with galactose. In this respect the present invention differs from the teaching according to EP 0 435 911 B1. In the cited patent specification it is proposed to use higher glutamine concentration (greater than 8 mM) in media, whereas the present invention claims preferably a reduced glutamine concentration, in particular a glutamine-free nutrient medium.

In EP 0 435 911 B1 (page 8, line 14, and page 14), the components succinate, malate, α-keto-glutarate, fumarate and citrate were tested as chelators for metal ions in a nutrient medium, in particular in a cell culture medium. On the basis of the experiments that were conducted, it was found that citrate is a good chelator for metal ions (page 22, claim 5). Apart from citrate, the other organic acids tested do not appear to have provided a satisfactory result. As the objective, in EP 0 435 911 B1, was to find a good metal chelator, very low concentrations of the organic acids tested were used (malate=10.7 mg/l, α-keto-glutarate=5.9 mg/l, succinate=0.96 mg/l, fumarate=0.88 mg/l). Moreover, in EP 0 435 911 B1 these substances are used explicitly in a medium with a glutamine concentration of more than 8 mM, because that is the invention of that specification. Another difference between the teaching of EP 0 435 911 B1 and of the present invention is that the substances according to the invention are used as modulators of metabolism. In this connection, the substances can preferably be used in a nutrient medium, in particular in a cell culture medium that contains carbohydrates and/or glutamine. The organic acids can, however, also preferably be used in a nutrient medium, in particular in a cell culture medium that does not contain any carbohydrates and/or does not contain glutamine. In EP 0 435 911 B1 the main energy and carbon sources of the cells are glucose and glutamine, so that the substances at the low concentration are of no significance as modulators of metabolism.

It was found, surprisingly, that in fact one of the best known metabolic byproducts of cells, namely lactate, promotes cell growth and the integral of viable cell concentration. It is stated in numerous works that lactate is a metabolic byproduct and is even said to be toxic to the cells. It was found, surprisingly, that lactate has a positive effect on cell growth, when the nutrient medium, in particular the cell culture medium, does not contain glutamine or contains a low concentration of glutamine, for example contains a glutamine concentration of less than 8 mM, or when glutamine has been replaced with glutamine-containing glutamine substitutes, or when the medium contains asparagine, especially when asparagine is present at higher concentration, e.g. the asparagine concentration is higher than 0.3 g/l, or when asparagine has been replaced with asparagine-containing substitutes, or when the medium contains glutamate, especially when the glutamate concentration is higher than 0.3 g/l, or when glutamate has been replaced with glutamate-containing substitutes, or the medium has been formulated with or without glucose, especially when the medium is glucose-free, in particular when the medium contains galactose. The positive effect of lactate is especially evident when the medium does not contain any glutamine and contains carbohydrates other than glucose as a source of carbon, especially when the medium contains galactose.

A preferred aspect of the invention therefore relates to a nutrient medium, in particular a cell culture medium, for the cultivation of a cell, or for obtaining a polypeptide, a protein or a vaccine (for example a virus) from organisms, in particular from cells or cell cultures, preferably from eukaryotic cells or cell cultures, where the organisms are cultivated in a suitable medium and the desired polypeptide or protein or vaccine is obtained from the organisms and/or the culture supernatant, characterized in that cell growth is stimulated by adding citric acid, succinic acid, malic acid, α-keto-glutaric acid, fumaric acid, oxalacetic acid, isocitric acid, oxalosuccinic acid, tartaric acid, adipic acid, lactic acid and mixtures thereof and salts or complexes of these acids in a nutrient medium, in particular in a cell culture medium.

A second preferred aspect of the invention relates to a method of cultivation of a cell, or for obtaining a polypeptide, a protein or a vaccine (for example a virus) from organisms, in particular from cells or cell cultures, preferably from eukaryotic cells or cell cultures, where the organisms are cultivated in a suitable medium and the desired polypeptide or protein or vaccine is obtained from the organisms and/or the culture supernatant, the method being characterized in that the organisms are brought into contact with a nutrient medium that contains at least one of the following substances: citric acid, succinic acid, malic acid, α-keto-glutaric acid, fumaric acid, oxalacetic acid, isocitric acid, oxalosuccinic acid, tartaric acid, adipic acid, lactic acid and mixtures thereof and salts or complexes of these acids.

The growth stimulation through addition of the aforementioned substances to the nutrient medium that is especially preferred according to this aspect of the invention is achieved because the nutrient medium has a low glutamine content, for example it has a glutamine concentration of less than 8 mM, preferably less than 5 mM, especially preferably less than 3 mM, most preferably less than 2 mM.

The growth stimulation through addition of the aforementioned substances to the nutrient medium, in particular to the cell culture medium, that is especially preferred according to this aspect of the invention, is achieved because the nutrient medium and/or feed medium is glutamine-free.

The growth stimulation through addition of the aforementioned substances to the nutrient medium that is especially preferred according to this aspect of the invention is achieved because the nutrient medium contains glutamine-containing glutamine substitutes. The concentration of glutamine-containing glutamine substitutes in the nutrient medium is then preferably at least 50 mg/l, more preferably at least 250 mg/l, especially preferably at least 500 mg/l, most preferably at least 1000 mg/l. The concentration of glutamine-containing glutamine substitutes in the nutrient medium is then preferably also at least 0.05 g/l, more preferably at least 0.2 g/l, especially preferably at least 0.8 g/l, most preferably at least 3.2 g/l.

The growth stimulation through addition of the aforementioned substances to the nutrient medium that is especially preferred according to this aspect of the invention is achieved because the nutrient medium contains asparagine or asparagine substitutes. The concentration of asparagine or asparagine substitutes in the nutrient medium is preferably at least 0.05 g/l, more preferably at least 0.15 g/l, especially preferably at least 0.3 g/l, most preferably at least 0.6 g/l. The growth stimulation through addition of the aforementioned substances to the nutrient medium that is especially preferred according to this aspect of the invention is achieved because the nutrient medium contains glutamate or glutamate substitutes. The concentration of glutamate or glutamate substitutes in the nutrient medium is preferably at least 0.05 g/l, more preferably at least 0.15 g/l, especially preferably at least 0.3 g/l, most preferably at least 0.6 g/l.

The growth stimulation through addition of the aforementioned substances to the nutrient medium that is especially preferred according to this aspect of the invention is achieved because the nutrient medium is glucose-free.

The growth stimulation through addition of the aforementioned substances to the nutrient medium that is especially preferred according to this aspect of the invention is achieved because the nutrient medium contains galactose. The galactose concentration is at least 0.1 g/l, preferably at least 1 g/l, especially preferably at least 5 g/l, most preferably at least 25 g/l. The growth stimulation through addition of the aforementioned substances to the nutrient medium that is especially preferred according to this aspect of the invention is achieved because the nutrient medium contains lactate. The lactate concentration is at least 0.1 g/l, preferably at least 1 g/l, especially preferably at least 5 g/l, most preferably at least 25 g/l.

The growth stimulation through addition of the aforementioned substances to the nutrient medium that is especially preferred according to this aspect of the invention is achieved because the nutrient medium and/or feed medium is free from glutamine or glutamine-containing substitutes.

The growth stimulation through addition of the aforementioned substances to the nutrient medium, in particular to the cell culture medium, that is especially preferred according to this aspect of the invention is achieved because the feed medium contains glutamine-containing glutamine substitutes. The concentration of glutamine-containing glutamine substitutes in the feed medium is preferably at least 0.2 g/l, more preferably at least 1 g/l, especially preferably at least 5 g/l, most preferably at least 10 g/l.

The growth stimulation through addition of the aforementioned substances to the nutrient medium, in particular to the cell culture medium, that is especially preferred according to this aspect of the invention is achieved because the feed medium contains asparagine or asparagine substitutes. The concentration of asparagine or asparagine substitutes in the feed medium is preferably at least 0.2 g/l, preferably at least 1 g/l, especially preferably at least 5 g/l, most preferably at least 10 g/l.

The growth stimulation through addition of the aforementioned substances to the nutrient medium, in particular to the cell culture medium, that is especially preferred according to this aspect of the invention is achieved because the feed medium contains glutamate or glutamate substitutes. The concentration of glutamate or glutamate substitutes in the feed medium is preferably at least 0.2 g/l, more preferably at least 1 g/l, especially preferably at least 5 g/l, most preferably at least 10 g/l.

The growth stimulation through addition of the aforementioned substances to the nutrient medium, in particular to the cell culture medium, that is especially preferred according to this aspect of the invention is achieved because the feed medium contains lactate or lactate derivatives. The concentration of lactate or lactate derivative in the feed medium is preferably at least 1 g/l, more preferably at least 5 g/l, especially preferably at least 25 g/l, most preferably at least 100 g/l.

The growth stimulation through addition of the aforementioned substances to the nutrient medium, in particular to the cell culture medium, that is especially preferred according to this aspect of the invention is achieved because the feed medium is glucose-free. The glucose concentration in the feed medium is preferably at most 100 g/l, preferably at most 25 g/l, especially preferably at most 5 g/l, most preferably at most 1 g/l.

The growth stimulation through addition of the aforementioned substances to the nutrient medium, in particular to the cell culture medium, that is especially preferred according to this aspect of the invention is achieved because the feed medium contains galactose. The galactose concentration in the feed medium is preferably at least 1 g/l, preferably at least 5 g/l, especially preferably at least 25 g/l, most preferably at least 100 g/l.

A third aspect of the invention relates to a cell or a cell culture, which is characterized in that the cell culture can survive or can divide in a medium with substances according to the invention or its peak cell density is increased, or its stationary phase is lengthened or its death phase is slowed down, or its formation of the byproducts of cell metabolism, for example ammonium or lactate, is reduced.

Owing to the stimulation of growth through the addition of the substances according to the invention to the nutrient medium, in particular to the cell culture medium, according to the invention, preferably in high-cell-density fermentation (highest total cell concentration attained during fermentation for example in particular $>1\times10^5$ cells/ml, preferably $>1\times10^6$ cells/ml in large-scale conditions (working volume >1 l, for example 30-20 000 l) the peak cell density can be increased, or the stationary phase can be lengthened, while cell vitality remains high for longer, i.e. the integral of viable cell concentration is increased and hence product yield is increased.

The method according to the invention is basically suitable for the production of any polypeptides, proteins or vaccines, for example for virus production. However, polypeptides that can be glycosylated or cannot be glycosylated are preferred. The polypeptides can for example be natural, human polypeptides or recombinant variants of human polypeptides.

The nutrient medium according to the invention is preferably suitable for the production of polypeptides with post-translational modifications, in particular for the production of glycoproteins. Addition of the substances according to the invention to a nutrient medium, in particular to a cell culture medium, can promote or inhibit particular glycosylation pathways and can therefore be favorable for the formation of a desired glycostructure of the desired polypeptide or of the vaccine. The substances according to the invention can, individually or in combination with one another, promote or inhibit a particular post-translational modification in the cell, with the result that the desired polypeptide variants or vaccine variants are expressed in production. For example the substances according to the invention can increase protein sialylation or protein galactosylation.

Through the use of the substances and nutrient media according to the invention, the variation in pH value of the cell cultivation process is very atypical at the upper end of the required value. It is usual in cell cultivation processes for the pH value of the process to start with pH 7.0 to pH 7.1, and for the cells to excrete acids, in particular lactate into the culture as a result of their metabolic activities. Therefore there is normally a shift of the pH value of the culture toward the acid range. It was found, surprisingly, that the pH value shifts toward more basic pH values when using the cell cultivation process according to the invention on account of the altered metabolism of the cells. Without being bound to the theory, this might be associated with the fact that the cells have a better metabolism and no longer excrete acids into the culture. Conversely, they metabolize acids. That is further evidence that the cells have a different metabolism owing to the substances and methods according to the invention. As a consequence, the pH value of the culture is at pH values above 7.2 (higher than pH 7.2 or to put it another way, more basic than pH 7.2). This is beneficial for protein glycosylation, for example, but not limited to this, for protein galactosylation or for protein sialylation. In their turn, some intracellular glycosylation enzymes are more active at pH values more basic than 7.2, leading to greater glycosylation of the proteins being produced. That is an important process property, resulting from the metabolism of the substances according to the invention.

Therefore a fourth aspect of the invention is a method of cultivation using the aforementioned culture media, in which the pH value of the cell cultivation process is preferably more basic than pH 7.2, in particular more basic than pH 7.3, more preferably more basic than pH 7.4, most preferably more basic than pH 7.5, very preferably more basic than pH 7.6, most preferably more basic than pH 7.7.

The method according to the invention is basically suitable for the cultivation of prokaryotic cells, for example bacteria, or eukaryotic cells, for example yeasts or animal cells. The term "animal cell" covers nonmammalian cells and mammalian cells. Examples of nonmammalian cells are cells of *Spodoptera frugiperda, Aedes aegypti, Aedes albopictus*. Preferred organisms for this invention are, however, mammalian cells. The mammalian cells can be primary cells, but permanent cell lines are preferred. The suitable permanent cell lines can for example be of human origin, for example PER-C6, human liver cells (Hep G2, HB 8065), human lung cells (W138, ATCC CCL 75), human cervical carcinoma cells (HeLa, ATCC CCL 2). The permanent cell lines can, however, also be of animal origin, for example derived from mouse or hamster, for example SV-40 immortalized monkey kidney cells (COS-7, ATCC CRL 1651), canine kidney cells (MDCK), monkey kidney cells (CV1, ATCC CCL 70), African green monkey kidney cells (VERO-76, ATCC CRL-1587), baby hamster kidney cells (BHK, ATCC CCL 10), Chinese hamster ovary cells (CHO-DG44, Urlaub and Chasin, Proc. Natl. Acad. Sci. USA, 1980, 77: 4216, or CHO-DUKX, or CHO-K1 with ATCC-number of ATCC CCL 61), lymphocytic cells (Jurkat T-cell line), buffalo rat liver cells (BRL 3A, ATCC CRL 1442), mouse mammary tumor cells (MMT 060562, ATCC CCL 51), SP2/0 cells, myeloma cells (for example NS0), hybridoma cells and trioma cells. The hybrid cell lines can originate from any species, including human and mouse. The descendants of the aforementioned cells are also suitable in cultivation in nutrient media according to the invention and methods according to the invention.

The cells that are preferred according to this invention are, however, from a mammalian cell line and are not hybridoma cells. The cell lines that are especially preferred according to the invention are all variants of the CHO, NS0, PERC-6 and BHK-21 cell lines, the cell lines being transformed with an exogenous nucleic acid, where the exogenous nucleic acid codes for the polypeptide of interest. "Exogenous nucleic acid" means a nucleic acid sequence that is not present in the host cell. The exogenous nucleic acid can also be homologous to a nucleic acid of the host cell, but which does not normally occur in this position in the host cell.

The cells that are preferred according to this invention are able to survive or to divide in the media with substances and methods according to the invention or their peak cell density is increased, or their stationary phase is lengthened or their death phase is slowed down, or their formation of byproducts of cell metabolism, for example ammonium or lactate, is reduced. The metabolism of the cells may be adapted in media with substances according to the invention or in methods according to the invention. This adaptation can take place through targeted molecular-biological alteration of the cells or through the adaptation of the cells in the media and methods according to the invention.

The term "clone" means a descendant of a parent cell, for example one of the cell lines enumerated above. A clone can arise when a cell possesses other cellular properties and so differs from the original parent cell. Usually clones can arise after a gene transfer of the parent cell, for example through transfection.

The term "metabolic optimization" means adaptation or change of cell metabolism to the desired conditions. The adaptation or change of cell metabolism can be achieved through targeted genetic intervention in the host cell, cloning certain genes into the cell, or switching-off certain genes. Or the adaptation or change of cell metabolism can be achieved when the cells are cultivated in the desired process conditions and/or in nutrient media, so that the cell itself adapts to the altered conditions. Through cultivation in the new conditions, novel cells can develop, which can be selected and isolated, which are genetically modified. The genetic modification is manifested for example as a change, in particular an improvement of cell metabolism. In particular, said cells with said altered cell metabolism grow especially well in comparison with conventional cells in the desired conditions, because their metabolism has been optimized.

A product according to the invention is a polypeptide, a protein or a virus, which is expressed in the cells and is harvested from the cultivation system, i.e. the cells and/or the cell medium. It can be any protein of interest. It can for example be diagnostic or therapeutic proteins, such as interleukins, enzymes, multimeric proteins or subunits of multimeric proteins, as well as antibodies or antibody fragments. The recombinant gene for the protein of interest can contain a signal sequence that is responsible for the excretion of the protein of interest from the host cell. The protein can be expressed from a transgenic promoter or its naturally active gene locus, and an immunoglobulin gene locus in hybridoma cells. The protein can also be expressed from a host-specific promoter, for example when a CHO cell is used for protein production, the foreign gene from a CHO promoter can be expressed. However, the product can also be a vaccine, for example a virus or virus-like particle, which is capable of replicating with the aid of a host cell. The cells to be cultivated can be adherent or can grow on microcarriers, but cells growing in suspension are preferred. Moreover, the cells can grow in serum-containing culture media (for example in fetal bovine serum, FBS, also called FCS), but a medium that does not contain serum and is called "serum-free" is preferred. Cells in serum-free media may need insulin and transferrin for optimal growth. Transferrin can be replaced at least partially with alternatives, for example with iron citrate. Most of the cell lines need one or more growth factors, comprising the recombinant polypetides or proteins as growth factor. The medium can contain polypeptides, but a low-polypeptide or a polypeptide-free or a protein-free medium is preferred. When the medium contains a polypeptide, a polypeptide produced by recombinant means is preferred. The medium can contain peptones, which can be of animal origin, but peptones of yeast origin are preferred, and peptones of plant origin are especially preferred. It is preferable to use culture media that are peptone-free and are fully defined chemically.

"Nutrient medium", also known as "culture medium" or "cell culture medium" by a person skilled in the art, means a medium that is used for the storage and/or cultivation of cell cultures or of at least one cell. A liquid nutrient medium, also called culture fluid, is preferred as the nutrient medium according to the invention. The term "nutrient medium" is used here as a generic term for all media. Nutrient medium comprises, for example, but is not limited to, the terms "basal medium" (culture medium), "feed medium" and "perfusion medium". A nutrient medium is thus a fluid that contains nutrients for cells. The substances according to the invention can be present in a nutrient medium together with other cellular nutrients. However, it is possible that the substances according to the invention are not present in a nutrient medium, and instead are added from another solution, for example from a stock solution to a nutrient medium with or without cells external to the culture. In this way the substances according to the invention do not come into contact with the cells directly via a nutrient medium, in particular via a cell culture medium, but indirectly. To that extent a method of contacting the cells with substances according to the invention is also a part of the invention.

"Nutrient medium", "culture medium" or "basal medium" means a medium, in particular a culture fluid, which promotes cell growth and/or cell vitality and/or product formation. The culture medium is preferably liquid.

Preferably, according to the invention, a high-cell-density cell culture medium is used, for supplying the necessary nutrients to a population of animal cells so as to reach, in a defined period of cultivation, a viable cell concentration of at least $1\times10^5$/ml, preferably at least $1\times10^6$/ml. Culture media that supply such high cell densities with nutrients are supplemented for example with the following substances: at least one amino acid, usually several amino acids and even all amino acids including cystine; at least one energy source, usually a source of carbohydrate, for example glucose, inorganic salts, vitamins, for example vitamin C and/or vitamin E; trace elements, also defined as inorganic components that are present at micromolar concentrations; buffers, up to four nucleosides or nucleotides, antioxidants and glutathione; lipids, for example cholesterol, phosphatidylcholine or lipid precursors for example choline or inositol. A high-cell-density medium preferably has at least one of the components enumerated above added to it, and can contain the components enumerated above at high concentrations.

The nutrient medium, in particular the cell culture medium, can optionally be supplemented with one or more or all components of the following categories:
a) Hormones and other growth factors, for example IGF-1, insulin, transferrin, epidermal growth factor
b) Salts and buffers, for example calcium, magnesium, and phosphates
c) Nucleosides and bases, for example adenosine, thymidine, hypoxanthine
d) Protein and tissue hydrolyzates.

The formulation of the culture media, to which substances according to the invention can be added, can preferably correspond to one of the published formulations. The formulations of the media can preferably be used in the published manner, but often they are modified and adapted to the requirements of the cell used. Examples of suitable published formulations of culture media are: Roswell Park Memorial Institute (RPMI) 1640 Medium, L-15 Medium, Dulbecco's Modified Eagle's Medium (DMEM), Eagle's Minimal Essential Medium (MEM), Ham's F12 Medium, or Iscoves' Modified DMEM. These published formulations of media can be used alone or mixed in any proportions as basal medium powder. The formulation of the culture media, to which the substances according to the invention can be added, can especially preferably be a commercial nutrient medium, whose recipe has not been published, for example, but not limited to, CD-CHO Medium from GIBCO, Ex-Cell 325 PF CHO Medium from Sigma (Cat. No.: 14340C).

"Feed medium" is a medium that is added to the cultivation system during cell cultivation, i.e. feed media are added to cultivation systems after the cells have come into contact with another medium, for example a culture medium (basal medium). Feed media contain substances that promote cell growth and/or cell vitality and/or product formation. By adding the feed media, the process time can be extended, because cell vitality can remain high for longer. The feed media can contain one or more energy sources, for example carbohydrates, for example glucose. Glucose can be contained in the feed medium or can be fed separately from another stock solution into the cultivation system. The feed medium can contain one or more amino acids. Feed media can only contain essential amino acids or only nonessential amino acids, or also a mixture of the two groups of amino acids. The feed medium can contain glutamine, or can be glutamine-free or can contain glutamine substitutes, or can contain glutamine-containing glutamine substitutes or can contain a mixture of glutamine and glutamine-containing glutamine substitutes. Glutamine can thus be combined in the feed medium with other substances, or can be fed separately from a stock solution as single substance into the cultivation system. Feed media can be just single concentrates of the basal medium, but feed media that are more than singly concentrated, for example doubly or more highly concentrated forms of the basal medium, are preferred. Feed media recipes are similar to basal media recipes, i.e. as a rule the feed media contain the same or a proportion of the substances that are present in basal media. Feed media can differ from basal media with respect to their inorganic components. They can for example be a basal medium without salts, or a low-salt variant of the basal medium. Feed media can, however, also include substances that are not present in basal media recipes.

"Glutamine-containing substances", "glutamine derivatives" or "glutamine-containing glutamine substitutes" mean substances that contain D- or L-glutamine, in particular L-glutamine in a molecule. This molecule can contain D- or L-glutamine in a great variety of ways, for example, but not limited to this, glutamine can be bound covalently to another substance. In particular, "glutamine-containing substances", "glutamine derivatives" or "glutamine-containing glutamine substitutes" mean peptides or oligopeptides from D- or L-glutamine (Roth, E. et al., In vitro cellular & developmental biology, 1988, 24(7): 696-698). For example, glutamine can be replaced with glutamine-based dipeptides, for example alanyl-glutamine (Ala-Gln) or glycyl-glutamine (Gly-Gln) (Christie, A. and Butler, M., Journal of Biotechnology, 1994, 37(3): 277-90; Sanfeliu, A. and Stephanopoulus, G., Biotechnol. and Bioeng., 1999, 64(1): 46-53; (Kurano, N., et al., J. Biotechnology, 1990, 15: 113-128). The term "glutamine-containing substances" is also described in WO 03/106661 (page 7, line 1).

"Asparagine substitutes", "asparagine derivatives" or "asparagine-containing asparagine substitutes" mean substances that contain D- or L-asparagine, in particular L-asparagine in a molecule. This molecule can contain D- or L-asparagine in a great variety of ways, for example, but not limited to this, asparagine can be bound covalently with another substance. In particular, "asparagine substitutes", "asparagine derivatives" or "asparagine-containing asparagine substitutes" mean peptides or oligopeptides from D- or L-asparagine. For example, but not limited to this, Leu-Asn (Sigma, catalog number: L0641), or Ile-Asn (Sigma catalog number: I3635), or Glu-Asn-Gly (Sigma, catalog number: P5148). The peptides can basically contain 2 or more than 2 amino acids.

"Glutamate substitutes", "glutamate derivatives" or "glutamate-containing glutamate substitutes" mean substances that contain D- or L-glutamate, in particular L-glutamate in a molecule. This molecule can contain D- or L-glutamate in a great variety of ways, for example, but not limited to this, glutamate can be bound covalently with another substance. In particular, "glutamate substitutes", "glutamate derivatives" or "glutamate-containing glutamate substitutes" mean peptides or oligopeptides from D- or L-glutamate. For example, but not limited to this, Asp-Glu (Sigma, catalog number: A1916-250MG), Glu-Glu (Sigma, catalog number: G3640-25MG), Glu-His (Sigma, catalog number: G6882-100MG), Glu-Leu (Sigma, catalog number: G7007-10MG), Glu-Lys (Sigma, catalog number: G5136-25MG). The peptides can basically contain 2 or more than 2 amino acids.

"Lactate substitutes", or "lactate-containing lactate substitutes" or "lactate derivatives" mean substances that contain D- or L-lactate in a molecule, for example, but not limited to this, iron(ll) lactate hydrate (Sigma, catalog number: 44953), or manganese(II) lactate trihydrate (Sigma, catalog number: 13227) or lactose. The molecule can contain D- or L-lactate in a great variety of ways, for example, but not limited to this, lactate can be bound to another substance, for example, but not limited to this, (+) ethyl D-lactate (Sigma, catalog number: 69796). Lactate derivatives are also molecules that can easily be converted intracellularly to lactate, for example, but not limited to this, pyruvate or alanine. In this case pyruvate can be added to the nutrient medium. Extracellular pyruvate is easily transported into the cell and converted to lactate by pyruvate dehydrogenase. In the case of alanine, extracellular alanine can be transported into the cell and converted to lactate by alanine transaminase via a pyruvate intermediate stage. This also applies to alanine-containing peptides, therefore alanine-containing peptides are also defined as "lactate derivatives".

The term "split ratio", also called "dilution factor", is a criterion for expressing the split ratio of two liquids. When two liquids are to be mixed together, in order to reach a target concentration, the solutions are mixed in proportions with a split ratio. Split ratio will be explained with the following example: a cell culture was inoculated in a culture vessel at a cell concentration of $2\times10^5$/ml and left to grow for 3 days. On the third day the cell concentration of $20\times10^5$/ml was measured. This culture is diluted with fresh medium, so that the target inoculation concentration of $2\times10^5$/ml is reached again. In this case the matured culture (inoculum) must be diluted 1:10 with fresh medium. If a working volume of 1 l is required in the new culture, it is necessary to use 100 ml inoculum and 900 ml fresh medium. In this case we would have a split ratio of 1:10.

All process variants in which cells are cultivated in order to produce a desired polypeptide, protein or a desired vaccine, are basically suitable for the application of the invention. However, a method that is preferred according to the invention is a high-cell-density method. The high-cell-density cell culture method is defined as a method in which, in a defined period of cultivation, a viable cell concentration of at least $1\times10^5$/ml, preferably at least $1\times10^6$/ml is reached, where the culture can be expanded by a single cell or by another cell culture or by an inoculum. Operating modes that are preferred according to the invention are continuous culture, fed-batch, batch, perfusion, or split-batch processes.

Cultivation is preferably carried out in a batch process, with all of the components for cell cultivation being placed in the culture vessel at the start of the process. In batch processes the cells are inoculated in a suitable medium and are harvested after a certain cultivation time. Then the desired product, for example a polypeptide, is isolated from the culture.

A method that is especially preferred according to the invention is a fed-batch process, in which the cells are brought into contact with another nutrient medium, for example with a feed medium, between inoculation and the end of the process.

A fed-batch process starts, for example, but not limited to this, with a basal medium. The cells are inoculated in the basal medium. After a certain time, for example, but not limited to this, 1-4 days after inoculation, the culture is contacted with another nutrient medium, for example this nutrient medium can be a feed medium. The feed medium can be added batchwise, at intervals or continuously at a set dose, to the cell culture. Therefore the volume of the culture increases during cultivation.

Another method of cultivation that is suitable according to the invention is perfusion, in which the cells, after a growth phase in a culture medium, are supplied with further fresh medium for example with perfusion medium, whereas the spent medium, with or without cells, is withdrawn from the process. Perfusion media may be different from culture media (basal media), or the same basal medium can also be used as perfusion medium. In perfusion methods the cells are first inoculated in a basal medium. In the course of cell cultivation, the cells (biomass) are separated from the cell culture (cell suspension) and on the one hand the spent medium is withdrawn from the process, and on the other hand new nutrients are made available to the cells through fresh medium. If cells are retained in the culture system during the process, this is called "perfusion". If cells are removed from the system with the spent medium during the process, this is called "continuous method". In perfusion processes, the cells can also be removed from the cultivation system at defined time intervals, so as to be able to maintain a maximum cell concentration. To a person skilled in the art, this operation is known as "bleeding". Cell separation is carried out with various technologies, with some technologies promoting cell separation indirectly.

Examples of some possible methods of cell separation are filtration, cell encapsulation, cell adherence to microcarriers, cell sedimentation or centrifugation.

Another suitable method according to the invention is the split-batch process (repeated batchwise operation) with or without feeding of the cells. In this method, after a growth phase a portion of the cell suspension is harvested and the rest of the cell suspension is left in the fermenter as inoculum of the next batch operation. The fermenter, with this inoculum, is then filled again to the desired working volume with fresh medium and the second batchwise operation thus begins.

The removal of samples from the cultivation system for offline measurements during the aforementioned operating modes has nothing to do with the method of cultivation that is described. Its only purpose is better understanding or control of the process.

The term "harvesting" or "cell harvesting" is an indication of the end of a production batch in an upstream process. In a batch and fed-batch process, the upstream process can only end with one harvest, whereas in split-batch, perfusion and in continuous methods there can be several harvests. Depending on the operating mode selected, the cell cultivation process (upstream process) can contain a lag phase, an exponential phase, a stationary phase and a death phase. The fermentation process can be ended in one of these growth phases. Preferably the fermentation process is ended in the stationary phase or in the death phase. At the end of the upstream process the cells are separated from the suspension. This cell separation process is called "harvesting" or "cell harvesting" here. Cell harvesting is followed by other purification steps so that the product can be isolated.

The term "inoculation" means the inoculating of a new cultivation system (for example a bioreactor and a suitable nutrient medium, in particular a cell culture medium) with cells. The inoculum, i.e. the cells or the cell suspension, are prepared beforehand for this purpose. Usually the cells that are to be inoculated are expanded before the actual production process, so that we have enough cells to be able to inoculate the new cultivation system with the desired cell concentration.

"Cell growth" means an increase in the viable cell concentration in at least one of the cultivation phases. The term "cell vitality" expresses the ratio of the viable cell concentration to the total cell concentration, which also includes the dead cells. This ratio can also be calculated in any way or means. One method is marking of the cells with a dye to differentiate the live and dead cells. One example for distinguishing between dead and live cells is the use of trypan blue dye. The marked cells are then counted and the number of dead and live cells is determined. Cell vitality is calculated by finding the ratio of the live cell count to the total cell count.

The term "osmolality" is a measure of the osmotic pressure of the dissolved particles in an aqueous solution. The dissolved particles include both the ions and the unionized molecules. Osmolality is expressed as the concentration of osmotically active particles, dissolved in 1 kg of water (1 mOsmol/kg $H_2O$ at 38° C. is equivalent to an osmotic pressure of 19 mmHg). The term "osmolarity" means the number of particles that are dissolved in 1 l of solution. Substances that occur in culture media and that increase the osmolality of the solution are therefore, for example, proteins, peptides, amino acids, unmetabolizable polymers, vitamins, ions, salts, sugars, metabolites, organic acids, lipids, etc.

The term "pH value" is the negative common logarithm of the numerical value of the molar hydrogen ion activity $a_{H}^{+}$ (pH=-log $a_{H}^{+}$). Solutions with a pH value of less than 7.0 have an acid reaction, with a pH value of 7.0 they are neutral. Solutions with a pH value greater than 7.0 have a basic reaction. When pH values of two solutions are compared, the solution with the higher pH value is defined as "more basic" relative to the solution with lower pH value, e.g. solution 1 has a pH value of 6.8, solution 2 has a pH value of 7.0. In this case solution 2 is more basic compared with solution 1. The pH values of the production processes can be measured in various ways. For example, but not limited to this, the pH value of a bioreactor can be measured on-line with a pH-electrode. Another method of determining the pH value of the culture is off-line sampling and detection of the pH value with an external pH-electrode.

Other advantageous embodiments are given in the subclaims.

BRIEF DECRIPTION OF THE DRAWINGS

The diagrams show:

FIG. 1: Growth data of metabolically optimized CHO cells in a nutrient medium according to the invention without glucose and without glutamine under routine strain maintenance.

Figure 2:
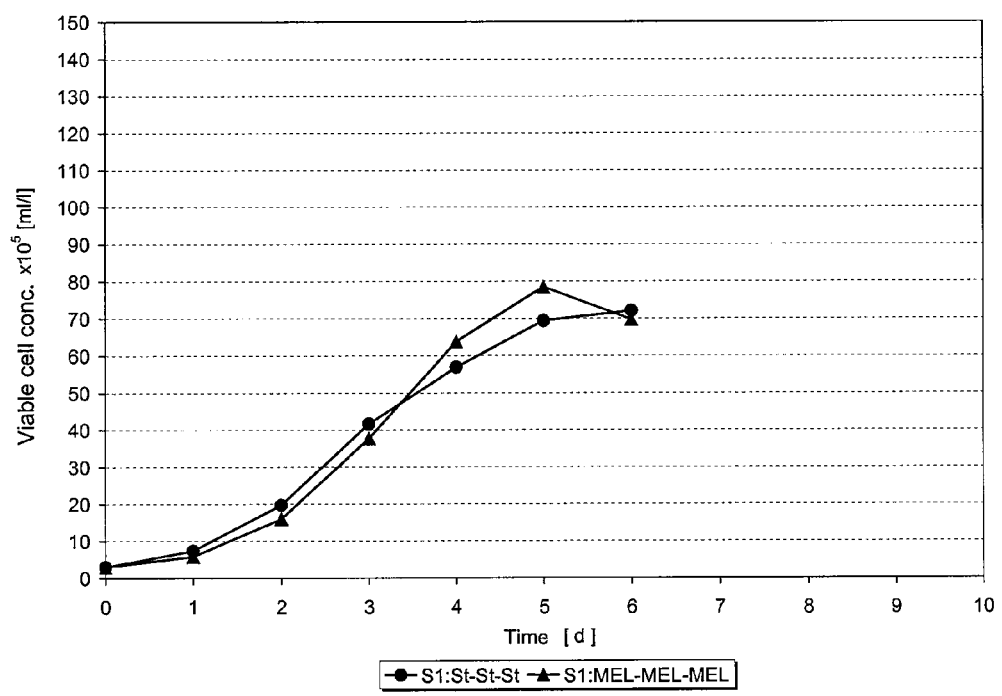

FIG. 2: Growth curve of cells in the nutrient medium according to the invention in comparison with a control in the fed-batch process.

Figure 3:
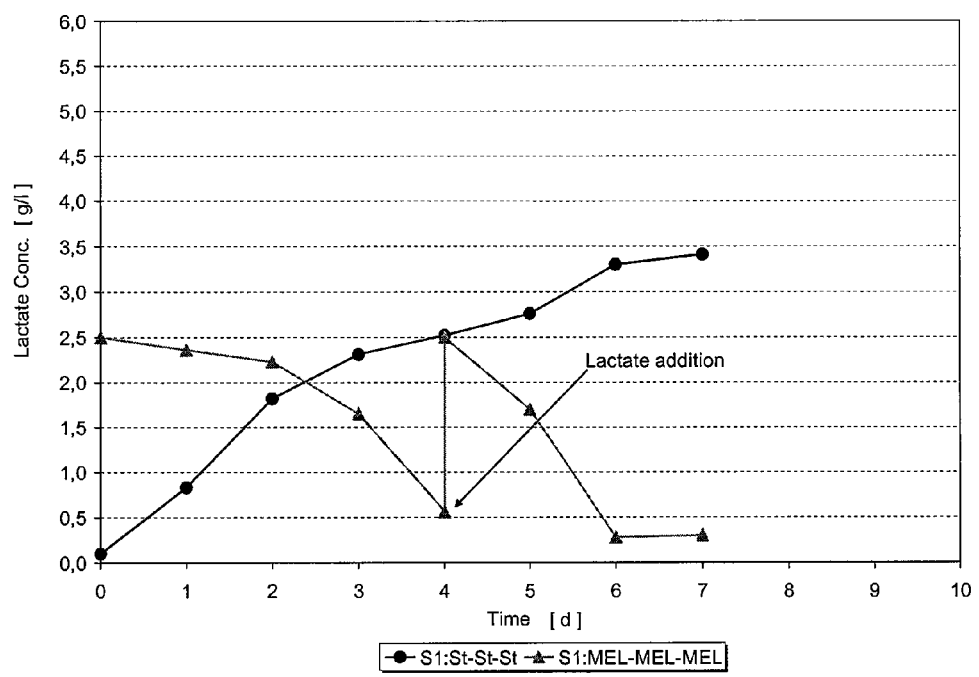

FIG. 3: Variation of lactate concentration during fed-batch cultivation.

Figure 4:
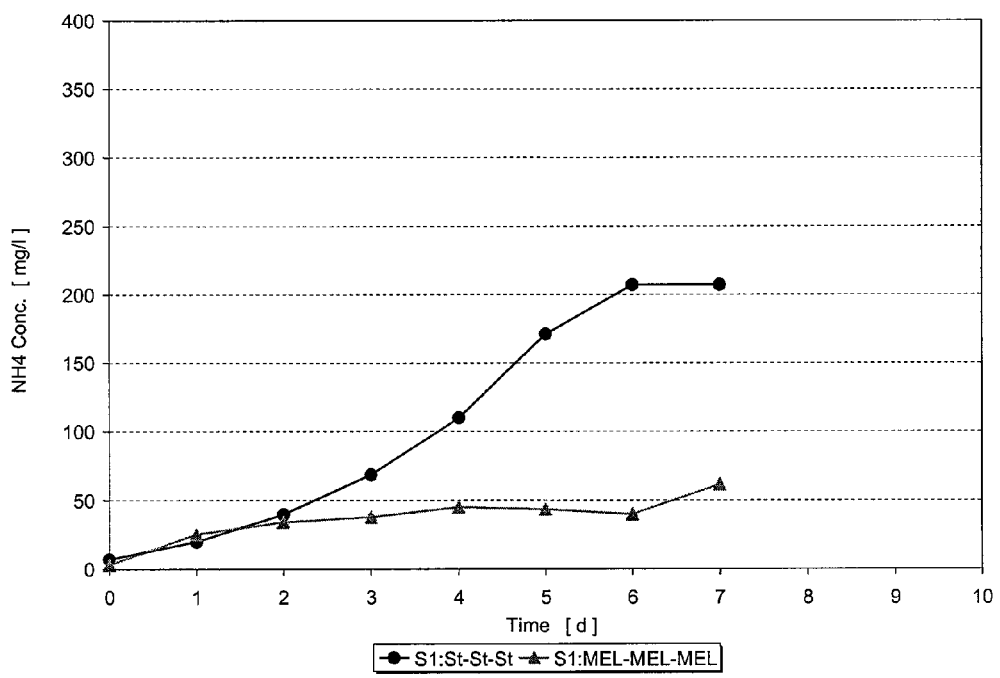

FIG. 4: Ammonium formation during fed-batch cultivation.

Figure 5:
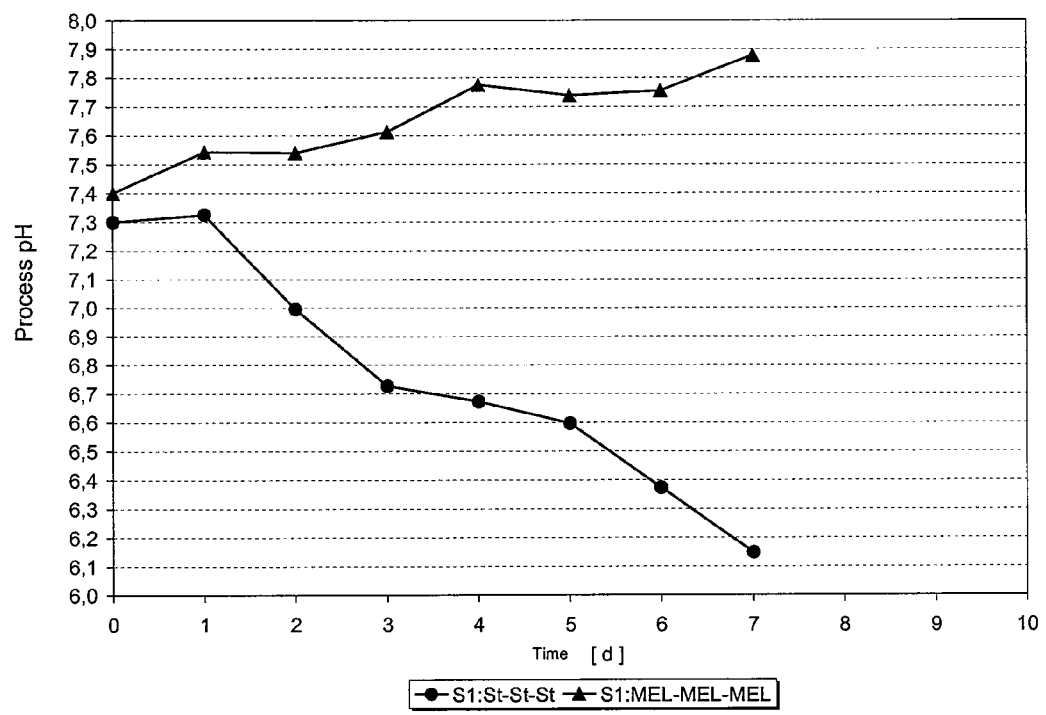

FIG. 5: Variation of the pH value of a cultivation process. The pH values were measured off-line and the pH value of the process was not regulated during cultivation.

Figure 6:
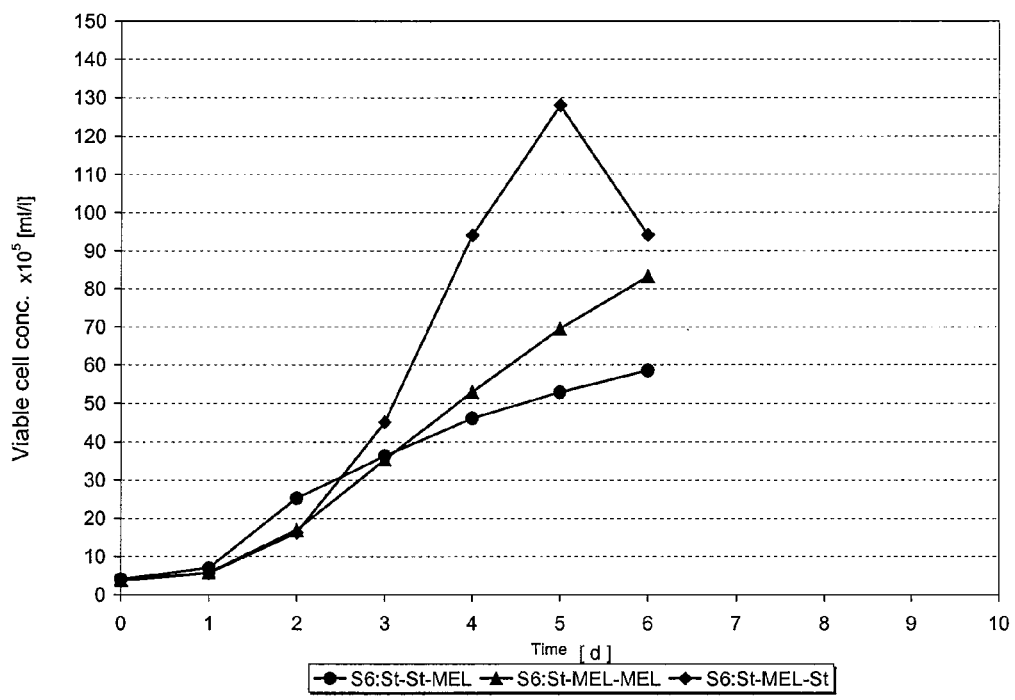

FIG. 6: Growth behavior of wild-type cells (metabolically unoptimized) in fed-batch cultivation with various combinations of basal media and feed media according to the invention.

Figure 7:
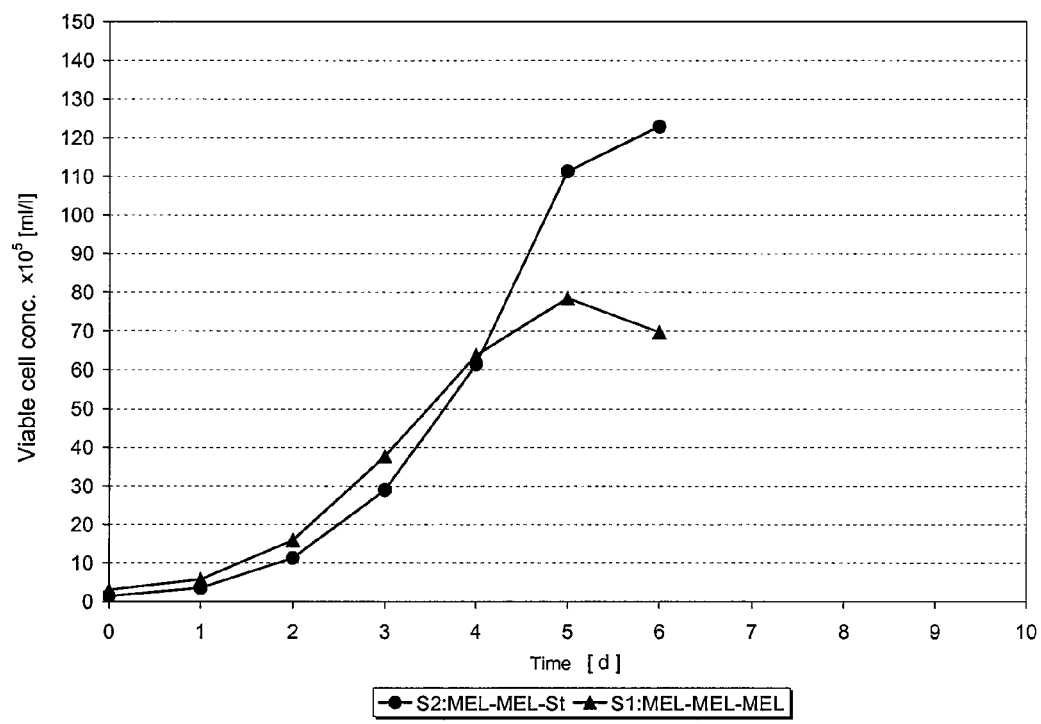

FIG. 7: Growth behavior of metabolically optimized cells in fed-batch cultivation in basal medium according to the invention and with 2 different feed media.

Figure 8:
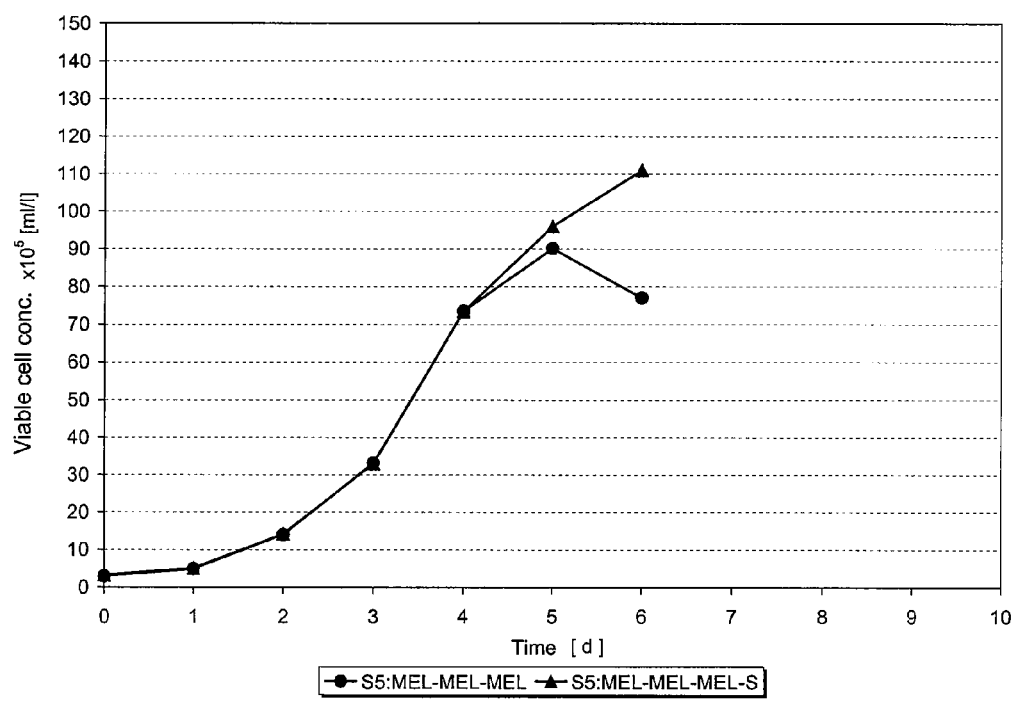

FIG. 8: Growth behavior of metabolically optimized cells in fed-batch cultivation in nutrient media according to the invention with and without sodium succinate.

FIG. 9: Variation of lactate concentration in nutrient media according to the invention with and without sodium succinate in fed-batch cultivation.

EXAMPLES

The invention is described in greater detail by use of the following examples, which are provided only for illustration and are not to be construed as limiting thie invention.
Material and Methods
Cell Culture Conditions Cells were stored in the gas phase of liquid nitrogen. One to two ampoules were thawed in nutrient medium preheated to 37° C. and transferred to spinner bottles, shaking flasks or T-bottles. In the first few days of cultivation the medium was changed, depending on the clone.

Depending on the clone, cells were split either every second day or every third day or after two and three days alternately into new medium, i.e. a portion of the cell suspension was removed from culture and a smaller portion of the cell suspension was reused as inoculum for the next culture. This inoculum was made up with fresh prewarmed nutrient medium. Cells were incubated at 37° C. in an incubator with a $CO_2$ atmosphere. An alternative for incubating cells was cultivation in an incubation chamber at 37° C., in this way cells were held in culture for several passages. A passage means a cultivation time of two to three days. At various points of time, cell suspension was taken from strain maintenance and used as inoculum for experiments. The experiments were carried out in various cultivation systems, for example in spinner bottles, T-bottles, shaking flasks, culture tubes or in controlled bioreactors.

A CHO cell line that expresses an antibody was used for the experiments. The product concentration (antibody concentration) in the cell supernatant was determined by ELISA.

A CHO medium from the company Sigma (CR 1020, Lot: 64K2403) was used as nutrient medium (basal medium) for the experiments. This is a serum-free, protein-free nutrient medium. It is a ready-made, sterile-filtered nutrient medium.

The experiments were carried out either in batch mode or in fed-batch mode. When the process was carried out in fed-batch mode, the process was first started in batch mode in the above-mentioned basal medium and cells were cultivated in this manner for 1-4 days. After 1-4 days the cells were supplemented with a feed medium, i.e. the process was switched to fed-batch mode. Feed took place at regular intervals. In fed-batch experiments, a protein-free and serum-free feed medium from the company HyQ (R05.2 supplement, Cat. No.: SH30584.04, Lot No.: APF21457G) was used.

All substances (chemicals) used according to the invention were obtained from the company Sigma and stock solutions were prepared from them. From the stock solutions, the substances were put at the desired final concentration in culture tubes. The various culture tubes prepared in this way were finally inoculated with the antibody-producing CHO-clone at a target inoculation cell concentration ($1-3 \times 10^5$/ml). For this, the corresponding amount of inoculum cells was calculated and the required amount of inoculum cell suspension was centrifuged. The cell pellet was finally taken up in the corresponding volume of fresh nutrient medium without substances according to the invention (Sigma, CR 1020, Lot: 64K2403). In this way the desired inoculation cell concentration was adjusted in the cell suspension being investigated. The cell suspension thus prepared was proportioned in the culture tubes, which were provided with the substances according to the invention beforehand. The culture tubes were incubated at 37° C., and 8% $CO_2$ atmosphere, with shaking. The culture tubes were cultivated for 8-11 days in the batch mode or in the fed-batch mode. Samples for offline measurement of the variables were taken from the culture vessels at regular intervals, for example daily or on every third day. The metabolic variables and cell concentrations of the samples were measured. Cell concentration and cell vitality were measured with a CeDex instrument. The metabolic variables (glucose, lactate, glutamine and ammonium) were determined with an analyzer (BioProfile 100).

Example 1

Batch Experiment with the Substances According to the Invention

The following final concentrations of the substances according to the invention were established in a nutrient medium after inoculation:

Sodium succinate at 1 g/l final concentration in the nutrient medium

Malic acid at 1 g/l final concentration in the nutrient medium

α-Keto-glutarate at 1 g/l final concentration in the nutrient medium

Sodium fumarate at 1 g/l final concentration in the nutrient medium

Tartaric acid at 0.5 g/l final concentration in the nutrient medium

Adipic acid at 0.5 g/l final concentration in the nutrient medium

Sodium lactate at 1 g/l final concentration in the nutrient medium

Ornithine at 1 g/l final concentration in the nutrient medium

Citrulline at 1 g/l final concentration in the nutrient medium

Sodium pyruvate at 0.5 g/l final concentration in the nutrient medium

The substances according to the invention were tested in batch mode. The nutrient medium or basal medium (serum-free, protein-free CHO medium from the company Sigma CR 1020, Lot: 64K2403) had a glucose concentration of 4.7 g/l and a glutamine concentration of 1.5 mM (Table 1).

TABLE 1

Results of the batch experiment with the substances according to the invention

| Time [d] | Viable Cell Density (VCD), [E5/ml] | Total Cell Density TCD, [E5/ml] | Viabil. [%] | Glucose [g/l] | Lactate [g/l] | NH4 [mM] | Gln [mM] | Specific glucose consumption (Gluc/VCD) | Specific lactate production (Lac/VCD) | Specific ammonia production (NH4/VCD) | Specific Glutamin consumption (Gln/VCD) | |
|---|---|---|---|---|---|---|---|---|---|---|---|---|
| 0 | 1.03 | 1.07 | 96 | 4.69 | 0 | 1.22 | 1.53 | 4.55 | 0.00 | 1.18 | 1.49 | Sodium succinate |
| 3 | 8.2 | 8.3 | 99 | 3.82 | 0.86 | 1.84 | 0.76 | 0.47 | 0.10 | 0.22 | 0.09 | |
| 6 | 48.1 | 49.1 | 98 | 2.4 | 1.19 | 2.25 | 0.31 | 0.05 | 0.02 | 0.05 | 0.01 | |
| 8 | 25.6 | 29.8 | 86 | 1.44 | 1.14 | 2.33 | 0.36 | 0.06 | 0.04 | 0.09 | 0.01 | |
| 11 | 16.3 | 32.8 | 50 | 0.22 | 1.59 | 3 | 0.52 | 0.01 | 0.10 | 0.18 | 0.03 | |
| 0 | 1.03 | 1.07 | 96 | 4.69 | 0 | 1.22 | 1.53 | 4.55 | 0.00 | 1.18 | 1.49 | Malic acid |
| 3 | 7.6 | 7.8 | 97 | 3.9 | 0.85 | 1.9 | 0.67 | 0.51 | 0.11 | 0.25 | 0.09 | |
| 6 | 42.2 | 43.4 | 97 | 2.65 | 1.14 | 2.42 | 0.28 | 0.06 | 0.03 | 0.06 | 0.01 | |
| 8 | 23.2 | 26.1 | 89 | 1.76 | 0.94 | 2.4 | 0.37 | 0.08 | 0.04 | 0.10 | 0.02 | |
| 11 | 17.5 | 28.5 | 61 | 0.47 | 1.2 | 2.75 | 0.44 | 0.03 | 0.07 | 0.16 | 0.03 | |
| 0 | 1.03 | 1.07 | 96 | 4.69 | 0 | 1.22 | 1.53 | 4.55 | 0.00 | 1.18 | 1.49 | α-Keto-glutarate |
| 3 | 7.1 | 7.2 | 99 | 4.24 | 0.56 | 1.81 | 0.73 | 0.60 | 0.08 | 0.25 | 0.10 | |
| 6 | 36.7 | 37.4 | 98 | 3.27 | 0.71 | 2.56 | 0.24 | 0.09 | 0.02 | 0.07 | 0.01 | |
| 8 | 22.2 | 23.9 | 93 | 2.19 | 0.62 | 2.65 | 0.36 | 0.10 | 0.03 | 0.12 | 0.02 | |
| 11 | 16.4 | 25.5 | 64 | 0.8 | 0.87 | 2.99 | 0.51 | 0.05 | 0.05 | 0.18 | 0.03 | |
| 0 | 1.03 | 1.07 | 96 | 4.69 | 0 | 1.22 | 1.53 | 4.55 | 0.00 | 1.18 | 1.49 | Sodium fumarate |
| 3 | 7 | 7.1 | 99 | 3.98 | 0.85 | 1.84 | 0.72 | 0.57 | 0.12 | 0.26 | 0.10 | |
| 6 | 40.6 | 41.5 | 98 | 2.61 | 1.19 | 2.49 | 0.24 | 0.06 | 0.03 | 0.06 | 0.01 | |

TABLE 1-continued

Results of the batch experiment with the substances according to the invention

| Time [d] | Viable Cell Density (VCD), [E5/ml] | Total Cell Density TCD, [E5/ml] | Viabil. [%] | Glucose [g/l] | Lactate [g/l] | NH4 [mM] | Gln [mM] | Specific glucose consumption (Gluc/VCD) | Specific lactate production (Lac/VCD) | Specific ammonia production (NH4/VCD) | Specific Glutamin consumption (Gln/VCD) | |
|---|---|---|---|---|---|---|---|---|---|---|---|---|
| 8 | 19.1 | 22.3 | 86 | 1.68 | 1.08 | 2.58 | 0.37 | 0.09 | 0.06 | 0.14 | 0.02 | |
| 11 | 14.3 | 26.2 | 55 | 0.46 | 1.46 | 3.06 | 0.47 | 0.03 | 0.10 | 0.21 | 0.03 | |
| 0 | 1.03 | 1.07 | 96 | 4.69 | 0 | 1.22 | 1.53 | 4.55 | 0.00 | 1.18 | 1.49 | Tartaric acid |
| 3 | 5.4 | 5.5 | 98 | 4.53 | 0.41 | 1.84 | 0.9 | 0.84 | 0.08 | 0.34 | 0.17 | |
| 6 | 40 | 41.3 | 97 | 3.56 | 0.6 | 2.89 | 0.19 | 0.09 | 0.02 | 0.07 | 0.00 | |
| 8 | 10.5 | 12.1 | 87 | 2.65 | 0.64 | 3.42 | 0.27 | 0.25 | 0.06 | 0.33 | 0.03 | |
| 11 | 8.7 | 18 | 48 | 1.71 | 0.79 | 3.87 | 0.42 | 0.20 | 0.09 | 0.44 | 0.05 | |
| 0 | 1.03 | 1.07 | 96 | 4.69 | 0 | 1.22 | 1.53 | 4.55 | 0.00 | 1.18 | 1.49 | Adipic acid |
| 3 | 7.1 | 7.2 | 99 | 4.28 | 0.62 | 1.81 | 0.86 | 0.60 | 0.09 | 0.25 | 0.12 | |
| 6 | 40.6 | 41.6 | 98 | 2.95 | 0.93 | 2.67 | 0.22 | 0.07 | 0.02 | 0.07 | 0.01 | |
| 8 | 14.9 | 17.1 | 87 | 1.94 | 0.95 | 3 | 0.32 | 0.13 | 0.06 | 0.20 | 0.02 | |
| 11 | 10.6 | 23 | 46 | 0.89 | 1.28 | 3.38 | 0.49 | 0.08 | 0.12 | 0.32 | 0.05 | |
| 0 | 1.03 | 1.07 | 96 | 4.69 | 0 | 1.22 | 1.53 | 4.55 | 0.00 | 1.18 | 1.49 | Sodium pyruvate |
| 3 | 7.7 | 7.8 | 99 | 4.55 | 0.38 | 1.72 | 1.02 | 0.59 | 0.05 | 0.22 | 0.13 | |
| 6 | 44 | 45 | 98 | 2.81 | 1.32 | 1.91 | 0.25 | 0.06 | 0.03 | 0.04 | 0.01 | |
| 8 | 21.6 | 24.5 | 88 | 1.79 | 1.34 | 2.23 | 0.38 | 0.08 | 0.06 | 0.10 | 0.02 | |
| 11 | 10.3 | 24.2 | 43 | 0.63 | 1.93 | 3.06 | 0.49 | 0.06 | 0.19 | 0.30 | 0.05 | |
| 0 | 1.03 | 1.07 | 96 | 4.69 | 1 | 1.22 | 1.53 | 4.55 | 0.97 | 1.18 | 1.49 | Sodium lactate |
| 3 | 6 | 6 | 100 | 4.44 | 1.15 | 1.65 | 1.12 | 0.74 | 0.19 | 0.28 | 0.19 | |
| 6 | 40.6 | 41 | 99 | 2.82 | 1.49 | 2.07 | 0.31 | 0.07 | 0.04 | 0.05 | 0.01 | |
| 8 | 21.3 | 23.7 | 90 | 1.79 | 1.47 | 2.63 | 0.35 | 0.08 | 0.07 | 0.12 | 0.02 | |
| 11 | 11.4 | 24.5 | 47 | 0.55 | 1.04 | 3.12 | 0.5 | 0.05 | 0.09 | 0.27 | 0.04 | |
| 0 | 1.03 | 1.07 | 96 | 4.69 | 0 | 1.22 | 1.53 | 4.55 | 0.00 | 1.18 | 1.49 | Ornithine |
| 3 | 6.3 | 6.5 | 97 | 4.24 | 0.71 | 1.82 | 0.92 | 0.67 | 0.11 | 0.29 | 0.15 | |
| 6 | 43.8 | 44.6 | 98 | 2.7 | 1.04 | 2.52 | 0.11 | 0.06 | 0.02 | 0.06 | 0.00 | |
| 8 | 19.8 | 22.3 | 89 | 1.82 | 0.97 | 2.72 | 0.37 | 0.09 | 0.05 | 0.14 | 0.02 | |
| 11 | 14.8 | 24.6 | 60 | 0.53 | 1.26 | 3.26 | 0.46 | 0.04 | 0.09 | 0.22 | 0.03 | |
| 0 | 1.03 | 1.07 | 96 | 4.69 | 0 | 1.22 | 1.53 | 4.55 | 0.00 | 1.18 | 1.49 | Citrulline |
| 3 | 7.5 | 7.7 | 97 | 4.14 | 0.83 | 1.87 | 0.82 | 0.55 | 0.11 | 0.25 | 0.11 | |
| 6 | 37.9 | 39.6 | 96 | 2.62 | 1.16 | 2.66 | 0.27 | 0.07 | 0.03 | 0.07 | 0.01 | |
| 8 | 14.6 | 17.8 | 82 | 1.7 | 1.12 | 2.86 | 0.37 | 0.12 | 0.08 | 0.20 | 0.03 | |
| 11 | 8.2 | 21.3 | 38 | 0.7 | 1.48 | 3.26 | 0.51 | 0.09 | 0.18 | 0.40 | 0.06 | |
| 0 | 1.03 | 1.07 | 96 | 4.69 | 0 | 1.22 | 1.53 | 4.55 | 0.00 | 1.18 | 1.49 | Control 1 |
| 3 | 7.9 | 8 | 99 | 4.32 | 0.79 | 1.84 | 0.92 | 0.55 | 0.10 | 0.23 | 0.12 | |
| 6 | 43.4 | 44.8 | 97 | 2.7 | 1.15 | 2.61 | 0.26 | 0.06 | 0.03 | 0.06 | 0.01 | |
| 8 | 16.8 | 19.6 | 86 | 1.74 | 1.11 | 2.83 | 0.37 | 0.10 | 0.07 | 0.17 | 0.02 | |
| 11 | 8.6 | 21.2 | 41 | 0.65 | 1.48 | 3.32 | 0.5 | 0.08 | 0.17 | 0.39 | 0.06 | |
| 0 | 1.03 | 1.07 | 96 | 4.69 | 0 | 1.22 | 1.53 | 4.55 | 0.00 | 1.18 | 1.49 | Control 2 |
| 3 | 7.2 | 7.4 | 97 | 4.34 | 0.76 | 1.83 | 0.94 | 0.60 | 0.11 | 0.25 | 0.13 | |
| 6 | 38.2 | 39.3 | 97 | 2.73 | 1.15 | 2.62 | 0.25 | 0.07 | 0.03 | 0.07 | 0.01 | |
| 8 | 16.9 | 19.6 | 86 | 1.76 | 1.11 | 2.84 | 0.36 | 0.10 | 0.07 | 0.17 | 0.02 | |
| 11 | 9.1 | 21.4 | 43 | 0.65 | 1.47 | 3.32 | 0.51 | 0.07 | 0.16 | 0.36 | 0.06 | |
| 0 | 1.03 | 1.07 | 96 | 4.69 | 0 | 1.22 | 1.53 | 4.55 | 0.00 | 1.18 | 1.49 | Mean value Control |
| 3 | 7.55 | 7.7 | 98 | 4.33 | 0.775 | 1.84 | 0.93 | 0.57 | 0.10 | 0.24 | 0.12 | |
| 6 | 40.8 | 42.05 | 97 | 2.715 | 1.15 | 2.62 | 0.255 | 0.07 | 0.03 | 0.06 | 0.01 | |
| 8 | 16.85 | 19.6 | 86 | 1.75 | 1.11 | 2.84 | 0.365 | 0.10 | 0.07 | 0.17 | 0.02 | |
| 11 | 8.85 | 21.3 | 42 | 0.65 | 1.475 | 3.32 | 0.505 | 0.07 | 0.17 | 0.38 | 0.06 | |

Example 2

Fed-Batch Experiment with the Substances According to the Invention

The following final concentrations of the substances according to the invention were established in a nutrient medium after inoculation:

Sodium succinate at 1 g/l final concentration in the nutrient medium

Malic acid at 1 g/l final concentration in the nutrient medium

α-Keto-glutarate at 1 g/l final concentration in the nutrient medium

Sodium fumarate at 1 g/l final concentration in the nutrient medium

Tartaric acid at 0.5 g/l final concentration in the nutrient medium

Adipic acid at 0.5 g/l final concentration in the nutrient medium

Sodium lactate at 1 g/l final concentration in the nutrient medium

Ornithine at 1 g/l final concentration in the nutrient medium

Sodium pyruvate at 0.5 g/l final concentration in the nutrient medium

In contrast to Example 1, the substances according to the invention were tested in fed-batch mode and two independent culture tubes were inoculated from each test substance (n=2).

The nutrient medium (serum-free, protein-free CHO medium from the company Sigma, CR 1020, Lot: 64K2403) had a glucose concentration of 4.7 g/l and a glutamine concentration of 0.7 mM. The feed medium used was from the company HyQ (R05.2 supplement, Cat. No.: SH30584.04, Lot No.: APF21457G). The feed medium was glutamine-free (Table 2).

TABLE 2

Results of the fed-batch experiment with the substances according to the invention

| Time [d] | Viable Cell Density (VCD), [E5/ml] | Total Cell Density TCD, [E5/ml] | Viabil. [%] | Glucose [g/l] | Lactate [g/l] | NH4 [mM] | Gln [mM] | Specific glucose consum. (Gluc/VCD) | Specific lactate prod. (Lac/VCD) | Specific ammonia prod. | Specific Glutamin consum. | |
|---|---|---|---|---|---|---|---|---|---|---|---|---|
| 0 | 1.37 | 1.50 | 91 | 4.65 | 0.00 | 1.04 | 0.70 | 3.39 | 0.00 | 0.76 | 0.51 | Mean value |
| 2 | 4.15 | 4.30 | 97 | 4.33 | 0.48 | 1.45 | 0.37 | 1.04 | 0.11 | 0.35 | 0.09 | of the controls |
| 5 | 12.70 | 13.20 | 96 | 6.97 | 1.10 | 2.01 | 0.00 | 0.55 | 0.09 | 0.16 | 0.00 | |
| 8 | 37.30 | 40.45 | 92 | 9.97 | 1.33 | 2.71 | 0.00 | 0.27 | 0.04 | 0.07 | 0.00 | |
| 0 | 1.37 | 1.5 | 91 | 4.65 | 0 | 1.04 | 0.7 | 3.39 | 0.00 | 0.76 | 0.51 | Sodium succinate |
| 2 | 4.1 | 4.2 | 98 | 3.91 | 0.46 | 1.36 | 0.42 | 0.95 | 0.11 | 0.33 | 0.10 | |
| 5 | Measument error | | ###### | 6.27 | 1.15 | 1.89 | 0 | #VALUE | #VALUE | #VALUE | #VALUE | |
| 8 | 55.7 | 62.2 | 90 | 8.44 | 1.34 | 2.41 | 0 | 0.15 | 0.02 | 0.04 | 0.00 | |
| 0 | 1.37 | 1.5 | 91 | 4.65 | 0 | 1.04 | 0.7 | 3.39 | 0.00 | 0.76 | 0.51 | Sodium succinate |
| 2 | 4.3 | 4.4 | 98 | 4.04 | 0.47 | 1.41 | 0.38 | 0.94 | 0.11 | 0.33 | 0.09 | |
| 5 | 17.5 | 18.1 | 97 | 6.63 | 1.18 | 1.92 | 0 | 0.38 | 0.07 | 0.11 | 0.00 | |
| 8 | 58.8 | 64.1 | 92 | 8.98 | 1.42 | 2.5 | 0 | 0.15 | 0.02 | 0.04 | 0.00 | |
| 0 | 1.37 | 1.5 | 91 | 4.65 | 0 | 1.04 | 0.7 | 3.39 | 0.00 | 0.76 | 0.51 | Malic acid |
| 2 | 3.8 | 3.9 | 97 | 4.09 | 0.45 | 1.41 | 0.38 | 1.08 | 0.12 | 0.37 | 0.10 | |
| 5 | 13.7 | 14.1 | 97 | 6.6 | 1.1 | 1.98 | 0 | 0.48 | 0.08 | 0.14 | 0.00 | |
| 8 | 44.9 | 49.1 | 91 | 9.2 | 1.32 | 2.63 | 0 | 0.20 | 0.03 | 0.06 | 0.00 | |
| 0 | 1.37 | 1.5 | 91 | 4.65 | 0 | 1.04 | 0.7 | 3.39 | 0.00 | 0.76 | 0.51 | Malic acid |
| 2 | 4.1 | 4.2 | 98 | 4.1 | 0.45 | 1.42 | 0.37 | 1.00 | 0.11 | 0.35 | 0.09 | |
| 5 | 12.5 | 12.8 | 98 | 6.7 | 1.09 | 1.98 | 0 | 0.54 | 0.09 | 0.16 | 0.00 | |
| 8 | 41.6 | 45.3 | 92 | 9.38 | 1.32 | 2.63 | 0 | 0.23 | 0.03 | 0.06 | 0.00 | |
| 0 | 1.37 | 1.5 | 91 | 4.65 | 0 | 1.04 | 0.7 | 3.39 | 0.00 | 0.76 | 0.51 | α-Keto-glutarate |
| 2 | 3.8 | 3.9 | 97 | 4.25 | 0.34 | 1.4 | 0.34 | 1.12 | 0.09 | 0.37 | 0.09 | |
| 5 | contamination | | ###### | | | | | #VALUE | #VALUE | #VALUE | #VALUE | |
| 0 | 1.37 | 1.5 | 91 | 4.65 | 0 | 1.04 | 0.7 | 3.39 | 0.00 | 0.76 | 0.51 | α-Keto-glutarate |
| 2 | 3.3 | 3.4 | 97 | 4.26 | 0.33 | 1.41 | 0.34 | 1.29 | 0.10 | 0.43 | 0.10 | |
| 5 | 11.4 | 11.8 | 97 | 7.15 | 0.76 | 1.91 | 0 | 0.63 | 0.07 | 0.17 | 0.00 | |
| 8 | 46.9 | 49.4 | 95 | 9.75 | 1.06 | 2.62 | 0 | 0.21 | 0.02 | 0.06 | 0.00 | |
| 0 | 1.37 | 1.5 | 91 | 4.65 | 0 | 1.04 | 0.7 | 3.39 | 0.00 | 0.76 | 0.51 | Sodium fumarate |
| 2 | 3.5 | 3.6 | 97 | 4.14 | 0.44 | 1.39 | 0.36 | 1.18 | 0.13 | 0.40 | 0.10 | |
| 5 | 13.4 | 13.9 | 96 | 6.79 | 1.13 | 1.95 | 0 | 0.51 | 0.08 | 0.15 | 0.00 | |
| 8 | 40.3 | 43.9 | 92 | 9.46 | 1.39 | 2.71 | 0 | 0.23 | 0.03 | 0.07 | 0.00 | |
| 0 | 1.37 | 1.5 | 91 | 4.65 | 0 | 1.04 | 0.7 | 3.39 | 0.00 | 0.76 | 0.51 | Sodium fumarate |
| 2 | 3.5 | 3.6 | 97 | 4.17 | 0.44 | 1.4 | 0.38 | 1.19 | 0.13 | 0.40 | 0.11 | |
| 5 | 12.8 | 13.2 | 97 | 6.75 | 1.12 | 1.95 | 0 | 0.53 | 0.09 | 0.15 | 0.00 | |
| 8 | 40.2 | 43.8 | 92 | 9.32 | 1.38 | 2.68 | 0 | 0.23 | 0.03 | 0.07 | 0.00 | |
| 0 | 1.37 | 1.5 | 91 | 4.65 | 0 | 1.04 | 0.7 | 3.39 | 0.00 | 0.76 | 0.51 | Tartaric acid |
| 2 | 3.9 | 4 | 98 | 4.37 | 0.32 | 1.46 | 0.38 | 1.12 | 0.08 | 0.37 | 0.10 | |
| 5 | 9.7 | 10.4 | 93 | 7.69 | 0.51 | 2.13 | 0 | 0.79 | 0.05 | 0.22 | 0.00 | |
| 8 | 23.7 | 26.6 | 89 | 11.22 | 0.69 | 2.98 | 0 | 0.47 | 0.03 | 0.13 | 0.00 | |
| 0 | 1.37 | 1.5 | 91 | 4.65 | 0 | 1.04 | 0.7 | 3.39 | 0.00 | 0.76 | 0.51 | Tartaric acid |
| 2 | 3.8 | 3.9 | 97 | 4.39 | 0.3 | 1.45 | 0.38 | 1.16 | 0.08 | 0.38 | 0.10 | |
| 5 | 9.1 | 9.6 | 95 | 7.34 | 0.5 | 2.12 | 0 | 0.81 | 0.05 | 0.23 | 0.00 | |
| 8 | 25 | 27.7 | 90 | 10.34 | 0.68 | 2.93 | 0 | 0.41 | 0.03 | 0.12 | 0.00 | |
| 0 | 1.37 | 1.5 | 91 | 4.65 | 0 | 1.04 | 0.7 | 3.39 | 0.00 | 0.76 | 0.51 | Adipic acid |
| 2 | 4.3 | 4.4 | 98 | 4.2 | 0.42 | 1.46 | 0.34 | 0.98 | 0.10 | 0.34 | 0.08 | |
| 5 | 11.7 | 12 | 98 | 7.33 | 0.88 | 2.04 | 0 | 0.63 | 0.08 | 0.17 | 0.00 | |
| 8 | 3.64 | 40 | 91 | 10.89 | 1.1 | 2.81 | 0 | 0.30 | 0.03 | 0.08 | 0.00 | |
| 0 | 1.37 | 1.5 | 91 | 4.65 | 0 | 1.04 | 0.7 | 3.39 | 0.00 | 0.76 | 0.51 | Adipic acid |
| 2 | 4.3 | 4.4 | 98 | 4.22 | 0.42 | 1.44 | 0.35 | 0.98 | 0.10 | 0.33 | 0.08 | |
| 5 | 11.2 | 11.8 | 95 | 7.26 | 0.88 | 2.03 | 0 | 0.65 | 0.08 | 0.18 | 0.00 | |
| 8 | 33.5 | 36.3 | 92 | 10.65 | 1.12 | 2.82 | 0 | 0.32 | 0.03 | 0.08 | 0.00 | |
| 0 | 1.37 | 1.5 | 91 | 4.65 | 0 | 1.04 | 0.7 | 3.39 | 0.00 | 0.76 | 0.51 | Sodium pyruvate |
| 2 | 3.1 | 3.2 | 97 | 4.4 | 0.27 | 1.42 | 0.4 | 1.42 | 0.09 | 0.46 | 0.13 | |
| 5 | 13.5 | 13.7 | 99 | 7.02 | 1.2 | 1.65 | 0 | 0.52 | 0.09 | 0.12 | 0.00 | |
| 8 | 41.5 | 46 | 90 | 9.44 | 1.8 | 2.43 | 0 | 0.23 | 0.04 | 0.06 | 0.00 | |
| 0 | 1.37 | 1.5 | 91 | 4.65 | 1 | 1.04 | 0.7 | 3.39 | 0.73 | 0.76 | 0.51 | Sodium lactate |
| 2 | 4.5 | 4.6 | 98 | 4.32 | 0.93 | 1.34 | 0.43 | 0.96 | 0.21 | 0.30 | 0.10 | |
| 5 | 12.8 | 13.1 | 98 | 7.03 | 1.47 | 1.85 | 0.05 | 0.55 | 0.11 | 0.14 | 0.00 | |
| 8 | 50.2 | 52.4 | 96 | 9.52 | 1.75 | 2.43 | 0.07 | 0.19 | 0.03 | 0.05 | 0.00 | |
| 0 | 1.37 | 1.5 | 91 | 4.65 | 1 | 1.04 | 0.7 | 3.39 | 0.73 | 0.76 | 0.51 | Sodium lactate |
| 2 | 3.8 | 4 | 95 | 4.34 | 0.93 | 1.35 | 0.43 | 1.14 | 0.24 | 0.36 | 0.11 | |
| 5 | 14 | 14.3 | 98 | 7.02 | 1.45 | 1.84 | 0.03 | 0.50 | 0.10 | 0.13 | 0.00 | |
| 8 | 52 | 54.7 | 95 | 9.45 | 1.73 | 2.41 | 0.05 | 0.18 | 0.03 | 0.05 | 0.00 | |
| 0 | 1.37 | 1.5 | 91 | 4.65 | 0 | 1.04 | 0.7 | 3.39 | 0.00 | 0.76 | 0.51 | Ornithine |
| 2 | 3.9 | 4 | 98 | 4.24 | 0.46 | 1.44 | 0.37 | 1.09 | 0.12 | 0.37 | 0.09 | |
| 5 | 11.9 | 12.4 | 96 | 6.96 | 1.03 | 2.01 | 0 | 0.58 | 0.09 | 0.17 | 0.00 | |
| 8 | 42.8 | 45.4 | 94 | 9.85 | 1.23 | 2.63 | 0 | 0.23 | 0.03 | 0.06 | 0.00 | |
| 0 | 1.37 | 1.5 | 91 | 4.65 | 0 | 1.04 | 0.7 | 3.39 | 0.00 | 0.76 | 0.51 | Ornithine |
| 2 | 3.8 | 3.9 | 97 | 4.26 | 0.45 | 1.44 | 0.38 | 1.12 | 0.12 | 0.38 | 0.10 | |
| 5 | 13.2 | 13.7 | 96 | 6.9 | 1.03 | 2 | 0 | 0.52 | 0.08 | 0.15 | 0.00 | |
| 8 | 36.8 | 39 | 94 | 9.72 | 1.23 | 2.63 | 0 | 0.26 | 0.03 | 0.07 | 0.00 | |

TABLE 2-continued

Results of the fed-batch experiment with the substances according to the invention

| Time [d] | Viable Cell Density (VCD), [E5/ml] | Total Cell Density TCD, [E5/ml] | Viabil. [%] | Glucose [g/l] | Lactate [g/l] | NH4 [mM] | Gln [mM] | Specific glucose consum. (Gluc/VCD) | Specific lactate prod. (Lac/VCD) | Specific ammonia prod. | Specific Glutamin consum. | |
|---|---|---|---|---|---|---|---|---|---|---|---|---|
| 0 | 1.37 | 1.5 | 91 | 4.65 | 0 | 1.04 | 0.7 | 3.39 | 0.00 | 0.76 | 0.51 | Control 1 |
| 2 | 4.1 | 4.3 | 95 | 4.32 | 0.48 | 1.45 | 0.36 | 1.05 | 0.12 | 0.35 | 0.09 | without additions |
| 5 | 13.8 | 14.4 | 96 | 7.05 | 1.09 | 2 | 0 | 0.51 | 0.08 | 0.14 | 0.00 | |
| 8 | 37.5 | 40.4 | 93 | 10.03 | 1.31 | 2.69 | 0 | 0.27 | 0.03 | 0.07 | 0.00 | |
| 0 | 1.37 | 1.5 | 91 | 4.65 | 0 | 1.04 | 0.7 | 3.39 | 0.00 | 0.76 | 0.51 | Control 2 |
| 2 | 4.2 | 4.3 | 98 | 4.33 | 0.47 | 1.45 | 0.37 | 1.03 | 0.11 | 0.35 | 0.09 | without additions |
| 5 | 11.6 | 12 | 97 | 6.89 | 1.11 | 2.02 | 0 | 0.59 | 0.10 | 0.17 | 0.00 | |
| 8 | 37.1 | 40.5 | 92 | 9.91 | 1.35 | 2.73 | 0 | 0.27 | 0.04 | 0.07 | 0.00 | |

From selected samples, the product concentration (antibody concentration) in the supernatant was determined by ELISA (Table 3)

TABLE 3

Result of product determination for the selected substances. The absolute value of the control was set at 100%.

| | Antibody concentration [%] |
|---|---|
| Control without additions | 100 |
| Sodium succinate B | 127 |
| Sodium lactate B | 124 |

Example 3

Fed-Batch Experiment with the Substances According to the Invention and Without Glutamine in All the Culture Media Used The following final concentrations of the substances according to the invention were established in a nutrient medium after inoculation:

Control, Without Additions

Sodium succinate at 1 g/l final concentration in the nutrient medium

α-Keto-glutarate at 1 g/l final concentration in the nutrient medium

Sodium lactate at 0.5 g/l final concentration in the nutrient medium

The substances according to the invention were tested under fed-batch conditions. The nutrient medium (serum-free, protein-free CHO medium from the company Sigma, CR 1020, Lot: 64K2403) had a glucose concentration of 4.7 g/l and it was glutamine-free. The feed medium used was from the company HyQ (R05.2 supplement, Cat. No.: SH30584.04, Lot No.: APF21457G). The feed medium was glutamine-free (Table 4).

TABLE 4

Results of the fed-batch experiment with the substances according to the invention in glutamine-free culture media

| Time [d] | VCD [% of control] | TCD [% of control] | Viabil. [%] | Sp. Gluc cons. | Sp. Lactate prod. [% of control] | Sp. NH4 prod [% of control] | |
|---|---|---|---|---|---|---|---|
| 0 | 100 | 100 | 94 | 100 | 100 | 100 | Control |
| 3 | 100 | 100 | 89 | 100 | 100 | 100 | without Gln |
| 5 | 100 | 100 | 91 | 100 | 100 | 100 | |
| 7 | 100 | 100 | 88 | 100 | 100 | 100 | |
| 9 | 100 | 100 | 93 | 100 | 100 | 100 | |
| 0 | 100 | 100 | 94 | 95 | — | 98 | Sodium succinate |
| 3 | 132 | 124 | 95 | 74 | 75 | 72 | without Gln |
| 5 | 111 | 108 | 95 | 88 | 93 | 90 | |
| 7 | 117 | 118 | 87 | 78 | 89 | 85 | |
| 9 | 136 | 134 | 94 | 69 | 78 | 74 | |
| 0 | 100 | 100 | 94 | 94 | — | 100 | alpha-Keto-glutarate |
| 3 | 103 | 94 | 96 | 98 | 70 | 94 | without Gln |
| 5 | 104 | 103 | 93 | 98 | 72 | 94 | |
| 7 | 99 | 96 | 90 | 95 | 72 | 95 | |
| 9 | 92 | 92 | 93 | 109 | 79 | 103 | |
| 0 | 100 | 100 | 94 | 93 | — | 98 | Sodium lactate |
| 3 | 148 | 140 | 94 | 66 | 72 | 63 | without Gln |
| 5 | 136 | 128 | 97 | 74 | 66 | 72 | |
| 7 | 147 | 136 | 95 | 62 | 57 | 66 | |
| 9 | 133 | 131 | 95 | 71 | 65 | 73 | |

Example 4

Fed-Batch Experiment with the Substances According to the Invention and with Glutamine-Containing Glutamine Substitutes The following final concentrations of the substances according to the invention were established in a nutrient medium after inoculation:

Control, Without Additions

Sodium succinate at 1 g/l final concentration in the nutrient medium

α-Keto-glutarate at 1 g/l final concentration in the nutrient medium

Sodium lactate at 0.5 g/l final concentration in the nutrient medium

The substances according to the invention were tested under fed-batch conditions. The nutrient medium (serum-free, protein-free CHO medium from the company Sigma, CR 1020, Lot: 64K2403) had a glucose concentration of 4.7 g/l and a glutamine concentration of 4 mM. The feed medium used was from the company HyQ (R05.2 supplement, Cat. No.: SH30584.04, Lot No.: APF21457G). 3 g/l alanyl-glutamine (Ala-Gln) and 3 g/l glycyl-glutamine (Gly-Gln) were added to the feed medium. The feed medium was glutamine-free (Table 5).

TABLE 5

Results of the fed-batch experiment with the substances according to the invention and with glutamine derivatives

| Time [d] | Viable Cell Density (VCD), [E5/ml] | Total Cell Density (TCD), [E5/ml] | Viabil. [%] | |
|---|---|---|---|---|
| 0 | 1.0 | 1.1 | 96 | Control |
| 3 | 7.9 | 8.2 | 96 | |
| 5 | 40.4 | 41.7 | 97 | |
| 7 | 21.0 | 37.2 | 56 | |
| 9 | 13.6 | 33.2 | 41 | |
| 0 | 1.0 | 1.1 | 96 | Sodium succinate |
| 3 | 8.8 | 9.3 | 95 | |
| 5 | 54.3 | 56.7 | 96 | |
| 7 | 34.5 | 42.0 | 82 | |
| 9 | 26.7 | 35.9 | 74 | |
| 0 | 1.0 | 1.1 | 96 | alpha-Keto-glutarate |
| 3 | 7.1 | 7.6 | 93 | |
| 5 | 38.5 | 40.1 | 96 | |
| 7 | 30.2 | 36.0 | 84 | |
| 9 | 21.0 | 31.2 | 67 | |
| 0 | 1.0 | 1.1 | 96 | Sodium lactate |
| 3 | 7.6 | 7.9 | 96 | |
| 5 | 43.3 | 45.2 | 96 | |
| 7 | 34.3 | 41.1 | 83 | |
| 9 | 25.2 | 34.7 | 73 | |

Example 5

Routine Cultivation of the Metabolically Optimized Cells in Strain Maintenance with Substances According to the Invention in a Glucose-Free and Glutamine-Free Nutrient Medium (Basal Medium)

A glucose-free and glutamine-free commercial nutrient medium was obtained. This medium was supplemented according to Table 6 with substances according to the invention to provide the final nutrient medium. The concentration of the substances shown in Table 6 is the final concentration of the respective substances in the medium. This nutrient medium corresponds to a serum-free, protein-free, peptone-free medium with substances according to the invention. The final nutrient medium for cell cultivation is thus glucose-free, glutamine-free, contains galactose and contains lactate.

TABLE 6

Composition of the nutrient medium (basal medium) for the routine cultivation of CHO cells with substances according to the invention in strain maintenance

| | | Glucose [g/l] | Galactose [g/l] | Lactate [g/l] | Glutamine [g/l] | Glutamate [g/l] | Asparagine [g/l] | Na-succinate [g/l] |
|---|---|---|---|---|---|---|---|---|
| MEL | Basal medium | 0 | 3 | 2.5 | 0 | 0.8 | 0.23 | 0 |

The metabolically optimized CHO cells were cultivated in shaking flasks under batch conditions for strain maintenance. Cells were inoculated in the aforementioned nutrient medium with an inoculation cell concentration of $1-2\times10^5$ live cells per ml. The culture was incubated at 37° C. and at 7.5% $pCO_2$ atmosphere for 2 days and the culture was subcultured on day 2. For this, on day 2 the cell concentration was counted and a cultivation vessel was inoculated with the same inoculation cell concentration in the same fresh medium. A cultivation period of two days was defined as one passage. The culture was cultivated in this way for several passages and the viable cell concentration was determined in each passage, shortly before subcultivation. The values found were plotted in a diagram (FIG. 1). It can be seen from FIG. 1 that the cells can grow well in the medium according to the invention. Cells have a doubling time of 17.9 hours in the medium according to the invention. Cells have a high split ratio of 1:6.3 in a cultivation mode of 2 days. If cells in strain maintenance are split every third day, they have a split ratio of more than 1:10. This high split ratio, or low doubling time is attained in a serum-free, protein-free, peptone-free, glucose-free, and glutamine-free medium.

Next, the second group of fed-batch experiments was carried out. The following materials and methods were used in all experiments starting from here (Examples 6 to 9):

The first nutrient medium that was used is a commercial nutrient medium (basal medium). This basal medium is a glucose-free and glutamine-free basal medium, whose recipe is not known. This basal medium was supplemented in the respective examples with substances according to the invention. The stated concentration of the substances in the examples is the final concentration of the respective substance in the basal medium. Therefore, if necessary, the nutrient media were supplemented with substances according to the invention until the stated final concentration was reached. After supplementation, the pH value of the basal medium was adjusted to 7.1±0.1. The osmolality of the basal medium was adjusted to 310±20 mOsmol/kg $H_2O$. Thus, the final basal medium was prepared and sterile-filtered. The basal medium prepared in this way corresponds to a serum-free, protein-free and peptone-free basal medium.

The second nutrient medium used is a feed medium. It is a serum-free, protein-free feed medium. The feed medium is of our own formulation, consisting inter alia of amino acids, salts and vitamins. This feed medium was supplemented with substances according to the invention in the respective examples. The stated concentration of the substances in the examples is the final concentration of the respective substance in the feed media. The final feed medium had a pH value of 6.0 to 7.8 and an osmolality of 460-750 mOsmol/kg $H_2O$.

All experiments were carried out in fed-batch conditions.

The experiments were started by inoculating the basal media with CHO cells. The inoculation cell concentration was 1-3 $10^5$/ml. The cultures were left to run for up to 7 days and were fed with the corresponding feed medium at regular intervals during cultivation.

The terminology used in the experiments is explained in the following examples. For example, name of the experiment S4:MEL-St-MEL.

S4: Number of the Experiment. It Varies from S1 to S6

First abbreviation (MEL): specification of the cells used. This can either be MEL (metabolically engineered), or St (standard, wild-type).

Second abbreviation (St): specification of the basal medium used. This can be either MEL (basal medium according to the invention), or St (standard basal medium).

Third abbreviation (MEL): specification of the feed medium used. This can be either MEL (feed medium according to the invention), or St (standard feed medium).

In the method according to the invention it was necessary to feed cells with lactate, as they need lactate as a source of carbohydrate. These feed media, or the cultures that had been fed with extra lactate, were noted in media tables with the comment "Extra feed". The reason is that lactate belongs to the stated feed media. However, lactate was not added to the feed media, in order to avoid solubility problems. Instead, the lactate concentration was determined daily and was added, if needed, (before the lactate limit) from a separate stock solution of the culture.

Example 6

Fed-Batch Experiment with the Substances According to the Invention, Without Glucose and Without Glutamine in Nutrient Media The following combination of media was used for this fed-batch experiment:

TABLE 7

| | Final concentration of the substances in the nutrient media used | | | | | |
|---|---|---|---|---|---|---|
| | Glucose [g/l] | Galactose [g/l] | Lactate [g/l] | Glutamine [g/l] | Glutamate [g/l] | Asparagine [g/l] |
| Basal medium of the control S1: St-St-St | 3.4 | 0 | 0 | 0.8 | 0.15 | 0.23 |
| Feed medium of the control S1: St-St-St | 60 | 0 | 0 | 13 | 0.15 | 0.15 |
| Basal medium of the experiment S1: MEL-MEL-MEL | 0 | 3 | 2.5 | 0 | 0.8 | 0.23 |
| Feed medium of the experiment S1: MEL-MEL-MEL | 0 | 60 | Extra feed | 0 | 7.15 | 0.15 |

S1: St-St-St = standard cell (wild-type cell), standard basal medium, standard feed medium
S1: MEL-MEL-MEL = metabolically optimized cell, basal medium according to the invention, feed medium according to the invention The results show that the metabolically optimized cells in nutrient media according to the invention display cell growth comparable to the control (FIG. 2). In contrast to the control, they produce less ammonium (FIG. 4) and they metabolize lactate, whereas the control produces lactate (FIG. 3). The pH value of the culture with substances according to the invention shifts to basic pH values (to higher pH values) or remains constant. The pH value of the control (conventional method) shifts to acid pH values (low pH value) (FIG. 5).

Example 7

The standard cell (wild-type cell, not genetically modified) was tested in fed-batch conditions with the following media combination:

TABLE 8

Final concentration of the substances in nutrient media that were used in this experiment

|  | Glucose [g/l] | Galactose [g/l] | Lactate [g/l] | Glutamine [g/l] | Glutamate [g/l] | Asparagine [g/l] |
|---|---|---|---|---|---|---|
| Basal medium of the experiment S6: St-St-MEL | 3.4 | 0 | 0 | 0.8 | 0.15 | 0.23 |
| Feed medium of the experiment S6: St-St-MEL | 0 | 35 | Extra feed | 0 | 5.15 | 6.15 |
| Basal medium of the experiment S6: St-MEL-MEL | 0 | 3 | 2.5 | 0 | 0.8 | 0.23 |
| Feed medium of the experiment S6: St-MEL-MEL | 0 | 35 | Extra feed | 0 | 5.15 | 6.15 |
| Basal medium of the experiment S6: St-MEL-St | 0 | 3 | 2.5 | 0 | 0.8 | 0.23 |
| Feed medium of the experiment S6: St-MEL-St | 60 | 0 | 0 | 13 | 0.15 | 0.15 |

S6: St-St-MEL = standard cell (wild-type cell), standard basal medium, feed medium according to the invention
S6: St-MEL-MEL = standard cell (wild-type cell), basal medium according to the invention, feed medium according to the invention
S6: St-MEL-St = standard cell (wild-type cell), basal medium according to the invention, standard feed medium In the prior art, several combinations of carbohydrates have been tested in basal media and feed media. All the combinations envisaged inoculation of the cells in a basal medium containing glucose. Then a fed-batch process was started, in which the feed medium contains e.g. galactose. The reason for this type of procedure is that the cells have a low growth rate in galactose-containing basal medium, or do not grow at all, therefore it was necessary to start with glucose-containing basal medium (Altamirano, C., et al., Biotechnol. Bioeng., 2001, 76(4): 351-60; Altamirano, C., et al., J. Biotechnology, 2004, 110(2): 171-9; Altamirano, C. et al., Biotechnol. Progress, 2000, 16(1): 69-75). According to the present invention, however, cell growth rate in galactose-containing medium is comparable to that in glucose-containing medium, so that a basal medium with substances according to the invention offers entirely new possibilities for cell cultivation. Therefore a basal medium according to the invention was combined here with various feed media.

It can be seen from the results that the feed medium according to the invention can be combined better with basal medium according to the invention (FIG. 6, comparison S6:St-St-MEL versus S6:St-MEL-MEL). The basal medium according to the invention can, however, be combined well with a standard feed medium, since the feed medium contains a carbohydrate other than galactose, e.g. glucose. Especially if the basal medium contains the substances according to the invention and the feed medium contains glucose, the cells grow to even higher cell concentration (FIG. 6, comparison S6:St-MEL-MEL versus S6:St-MEL-St).

A similar experiment was also carried out with metabolically optimized cells (FIG. 7). The nutrient media of the fed-batch experiment with metabolically optimized cells were as follows:

TABLE 9

Final concentration of the substances in the nutrient media that were used in this experiment

|  | Glucose [g/l] | Galactose [g/l] | Lactate [g/l] | Glutamine [g/l] | Glutamate [g/l] | Asparagine [g/l] |
|---|---|---|---|---|---|---|
| Basal medium of the experiment S1: MEL-MEL-MEL | 0 | 3 | 2.5 | 0 | 0.8 | 0.23 |
| Feed medium of the experiment S1: MEL-MEL-MEL | 0 | 60 | Extra feed | 0 | 7.15 | 0.15 |
| Basal medium of the experiment S2: MEL-MEL-St | 0 | 3 | 2.5 | 0 | 0.8 | 0.23 |
| Feed medium of the experiment S2: MEL-MEL-St | 60 | 0 | 0 | 13 | 0.15 | 0.15 |

S1: MEL-MEL-MEL = metabolically optimized cell, basal medium according to the invention, feed medium according to the invention
S2: MEL-MEL-St = metabolically optimized cell, basal medium according to the invention, standard feed medium Example 9

Fed-Batch Experiment with Two Substances According to the Invention in Nutrient Media In this experiment, 2 substances according to the invention (lactate and succinate) were combined together in a fed-batch experiment. The following nutrient media combination was used for this fed-batch experiment:

TABLE 10

| | Glucose [g/l] | Galactose [g/l] | Lactate [g/l] | Glutamine [g/l] | Glutamate [g/l] | Asparagine [g/l] | Na-succinate [g/l] |
|---|---|---|---|---|---|---|---|
| Final concentration of the substances used in nutrient media of this experiment | | | | | | | |
| Basal medium of the experiment S5: MEL-MEL-MEL | 0 | 3 | 2 | 0 | 0.8 | 0.23 | 0 |
| Feed medium of the experiment S5: MEL-MEL-MEL | 0 | 35 | Extra feed | 0 | 5 | 6.15 | 0 |
| Basal medium of the experiment S5: MEL-MEL-MEL-S | 0 | 3 | 2 | 0 | 0.8 | 0.23 | 0.5 |
| Feed medium of the experiment S5: MEL-MEL-MEL-S | 0 | 35 | Extra feed | 0 | 5 | 6.15 | 5 |

S5: MEL-MEL-MEL = metabolically optimized cell, basal medium according to the invention with lactate, feed medium according to the invention with lactate
S5: MEL-MEL-MEL-S = metabolically optimized cell, basal medium according to the invention with lactate and succinate, feed medium according to the invention with lactate and succinate FIG. 8 shows the growth behavior of the metabolically optimized cells in nutrient media according to the invention with and without sodium succinate. FIG. 9 shows the variation of lactate concentration in the nutrient media according to the invention with and without sodium succinate.

What is claimed is:

1. A cell line nutrient medium for the cultivation of a cell line, wherein the cell line nutrient medium contains at least one substance selected from the group consisting of succinic acid and salts and complexes of succinic acid, wherein the cell line nutrient medium contains glutamine at a concentration of less than 8 mmol/l, wherein the nutrient medium contains the at least one substance at a concentration of at least 0.2 g/l and at most 100 g/l and wherein the cell line nutrient medium is protein-free.

2. The nutrient medium according to claim 1, wherein the nutrient medium contains the at least one substance at a concentration of at least 0.3 g/l and at most 50g/l.

3. The nutrient medium according to claim 1, wherein the nutrient medium is glucose-free.

4. The nutrient medium according to claim 1, wherein the nutrient medium is glutamine-free.

5. The nutrient medium according to claim 1, wherein the nutrient medium is a liquid nutrient medium.

6. The nutrient medium according to claim 1, wherein the nutrient medium is a basal medium with an osmolality of 240 to 360 mOsmol/kg $H_2O$.

7. The nutrient medium according to claim 1, wherein the nutrient medium is a feed medium with an osmolality of 150 to 1500 mOsmol/kg $H_2O$.

8. The nutrient medium according to claim 1, wherein the nutrient medium contains the at least one substance at a concentration of at least 1 g/l and at most 25 g/l.

* * * * *

UNITED STATES PATENT AND TRADEMARK OFFICE
CERTIFICATE OF CORRECTION

PATENT NO.         : 8,426,202 B2  
APPLICATION NO. : 12/067878  
DATED              : April 23, 2013  
INVENTOR(S)       : Aziz Cayli Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 445 days.

Signed and Sealed this
Eighth Day of September, 2015

Michelle K. Lee
*Director of the United States Patent and Trademark Office*